(12) United States Patent
Brunnett et al.

(10) Patent No.: US 10,016,276 B2
(45) Date of Patent: Jul. 10, 2018

(54) RETAINING MECHANISMS FOR PROSTHETIC HEART VALVES

(71) Applicant: Edwards Lifesciences Corporation, Irvine, CA (US)

(72) Inventors: William C. Brunnett, Mission Viejo, CA (US); Charles Stanislaus, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 110 days.

(21) Appl. No.: 14/441,825

(22) PCT Filed: Nov. 20, 2013

(86) PCT No.: PCT/US2013/070953
§ 371 (c)(1),
(2) Date: May 8, 2015

(87) PCT Pub. No.: WO2014/081796
PCT Pub. Date: May 30, 2014

(65) Prior Publication Data
US 2015/0282931 A1    Oct. 8, 2015

Related U.S. Application Data

(60) Provisional application No. 61/729,109, filed on Nov. 21, 2012.

(51) Int. Cl.
*A61F 2/24* (2006.01)
(52) U.S. Cl.
CPC .......... *A61F 2/2445* (2013.01); *A61F 2/2412* (2013.01); *A61F 2/2418* (2013.01);
(Continued)

(58) Field of Classification Search
CPC ........ A61F 2/24; A61F 2/2418; A61F 2/2445; A61F 2/852; A61F 2/07; A61F 2250/0063
(Continued)

(56) References Cited

U.S. PATENT DOCUMENTS 3,409,013 A   11/1968  Berry
3,467,101 A    9/1969  Fogarty et al.
(Continued)

FOREIGN PATENT DOCUMENTS

CA    2436258 A1    1/2005
CA    2627555 A1    5/2007
(Continued)

OTHER PUBLICATIONS

Int'l. Search Report for PCT/US2013/070953, dated Mar. 6, 2014.
(Continued)

*Primary Examiner* — Kathleen Holwerda
(74) *Attorney, Agent, or Firm* — Thomas C. Richardson

(57) ABSTRACT

According to one representative embodiment, a method of treating aortic insufficiency comprises delivering a support structure to a position around the leaflets of a native heart valve. The support structure comprises an annular body defining an interior and at least one projection extending radially inwardly from the annular body. An expandable prosthetic heart valve can be advanced into the native heart valve and into the interior of the annular body. The prosthetic heart valve can be expanded into contact with the leaflets of the native valve, thereby causing the leaflets of the native valve to be frictionally secured between an inner surface of the annular body and an outer surface of the prosthetic heart valve and causing the at least one projection and a portion of one of the leaflets contacted by the at least one projection to extend into an opening of the frame of the prosthetic valve.

14 Claims, 21 Drawing Sheets

(52) U.S. Cl.
CPC .......... *A61F 2/2433* (2013.01); *A61F 2/2436* (2013.01); *A61F 2/2466* (2013.01); *A61F 2230/0069* (2013.01); *A61F 2250/0063* (2013.01)

(58) Field of Classification Search
USPC .................................. 606/153; 623/1.11–1.54
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,347,057 A * | 8/1982 | Yasnitsky .............. D06M 11/64 8/116.1 |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,383,905 A | 1/1995 | Golds et al. |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goecoechea et al. |
| 6,350,277 B1 | 2/2002 | Kocur |
| 6,425,916 B1 * | 7/2002 | Garrison ............... A61F 2/2418 623/1.26 |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,520,984 B1 * | 2/2003 | Garrison ................... A61F 2/07 623/1.11 |
| 6,527,979 B2 | 3/2003 | Constantz et al. |
| 6,569,196 B1 | 5/2003 | Vesely et al. |
| 6,582,462 B1 | 6/2003 | Andersen et al. |
| 6,605,112 B1 | 8/2003 | Moll |
| 6,652,578 B2 | 11/2003 | Bailey et al. |
| 6,730,118 B2 | 5/2004 | Spenser et al. |
| 6,733,525 B2 | 5/2004 | Yang et al. |
| 6,752,813 B2 | 6/2004 | Goldfarb et al. |
| 6,767,362 B2 | 7/2004 | Schreck |
| 6,830,584 B1 | 12/2004 | Seguin |
| 6,878,162 B2 | 4/2005 | Bales et al. |
| 6,893,459 B1 | 5/2005 | Macoviak |
| 6,893,460 B2 | 5/2005 | Spenser et al. |
| 6,908,481 B2 | 6/2005 | Cribier |
| 7,011,681 B2 | 3/2006 | Vesely |
| 7,018,406 B2 | 3/2006 | Seguin et al. |
| 7,018,408 B2 | 3/2006 | Bailey et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |

(56) References Cited

U.S. PATENT DOCUMENTS

| | | |
|---|---|---|
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,497,872 B2* | 3/2009 | Melsheimer .............. A61F 2/07 623/1.13 |
| 7,510,575 B2 | 3/2009 | Spenser et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,655,034 B2 | 2/2010 | Mitchell et al. |
| 7,722,666 B2 | 5/2010 | Lafontaine |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,323,335 B2 | 12/2012 | Rowe et al. |
| 8,328,868 B2 | 12/2012 | Paul et al. |
| 8,449,606 B2 | 5/2013 | Eliasen et al. |
| 8,652,203 B2 | 2/2014 | Quadri et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0036791 A1 | 2/2003 | Philipp et al. |
| 2003/0050694 A1 | 3/2003 | Yang et al. |
| 2003/0100393 A1 | 5/2003 | Nanko |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0127982 A1 | 7/2004 | Machold et al. |
| 2004/0186563 A1 | 9/2004 | Lobbi |
| 2004/0186565 A1 | 9/2004 | Schreck |
| 2004/0215324 A1* | 10/2004 | Vonderwalde ............ A61F 2/07 623/1.15 |
| 2004/0220655 A1 | 11/2004 | Swanson et al. |
| 2004/0243230 A1 | 12/2004 | Navia et al. |
| 2004/0260389 A1 | 12/2004 | Case et al. |
| 2005/0033362 A1* | 2/2005 | Grafton ............ A61B 17/06166 606/228 |
| 2005/0096736 A1 | 5/2005 | Osse et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0197696 A1 | 9/2005 | Gomez Duran |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0149350 A1 | 7/2006 | Patel et al. |
| 2006/0195134 A1 | 8/2006 | Crittenden |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0265700 A1 | 11/2007 | Eliasen et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1* | 4/2008 | Styrc ............... A61F 2/2418 623/2.18 |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0262592 A1 | 10/2008 | Jordan et al. |
| 2009/0054968 A1 | 2/2009 | Bonhoeffer et al. |
| 2009/0062908 A1 | 3/2009 | Bonhoeffer et al. |
| 2009/0093876 A1 | 4/2009 | Nitzan et al. |
| 2009/0157175 A1 | 6/2009 | Benichou |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0222076 A1 | 9/2009 | Figulla et al. |
| 2009/0254165 A1 | 10/2009 | Tabor et al. |
| 2009/0276040 A1 | 11/2009 | Rowe et al. |
| 2009/0281609 A1 | 11/2009 | Benichou et al. |
| 2009/0281619 A1 | 11/2009 | Le et al. |
| 2009/0287299 A1 | 11/2009 | Tabor et al. |
| 2009/0319037 A1* | 12/2009 | Rowe ............... A61F 2/2418 623/2.11 |
| 2010/0016958 A1 | 1/2010 | St. Goar et al. |
| 2010/0049313 A1 | 2/2010 | Alon et al. |
| 2010/0057193 A1 | 3/2010 | Carpentier et al. |
| 2010/0168844 A1 | 7/2010 | Toomes et al. |
| 2010/0198347 A1 | 8/2010 | Zakay et al. |
| 2010/0286768 A1 | 11/2010 | Alkhatib |
| 2011/0015729 A1 | 1/2011 | Jimenez et al. |
| 2011/0071614 A1* | 3/2011 | Majercak ............ A61F 2/07 623/1.14 |
| 2011/0270374 A1 | 11/2011 | Orr et al. |
| 2012/0022633 A1* | 1/2012 | Olson ............... A61F 2/2418 623/1.11 |
| 2012/0053681 A1 | 3/2012 | Alkhatib et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0190857 A1 | 7/2013 | Mitra et al. |
| 2013/0274873 A1 | 10/2013 | Delaloye et al. |
| 2013/0310928 A1* | 11/2013 | Morriss ............... A61F 2/2418 623/2.12 |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |

FOREIGN PATENT DOCUMENTS

| | | |
|---|---|---|
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 20221871 U1 | 9/2008 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |

(56) References Cited

FOREIGN PATENT DOCUMENTS

| | | |
|---|---|---|
| EP | 1088529 A2 | 4/2001 |
| EP | 1281375 A2 | 2/2003 |
| EP | 1570809 A1 | 9/2005 |
| EP | 1629795 A1 | 3/2006 |
| EP | 1796597 A2 | 6/2007 |
| FR | 2788217 A1 | 7/2000 |
| FR | 2815844 A1 | 5/2002 |
| FR | 2828263 A1 | 2/2003 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 93/01768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/62189 A1 | 8/2001 |
| WO | 0154624 A1 | 8/2001 |
| WO | 0154625 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 05/034812 | 4/2005 |
| WO | 2005/087140 A1 | 9/2005 |
| WO | 2005084595 A1 | 9/2005 |
| WO | 05/102015 | 11/2005 |
| WO | 2006/014233 A2 | 2/2006 |
| WO | 2006/034008 A2 | 3/2006 |
| WO | 06/111391 | 10/2006 |
| WO | 06/138173 | 12/2006 |
| WO | 2007047488 A2 | 4/2007 |
| WO | 2007067942 A1 | 6/2007 |
| WO | 2007097983 A2 | 8/2007 |
| WO | 2008/005405 A2 | 1/2008 |
| WO | 2008015257 A2 | 2/2008 |
| WO | 2008/035337 A2 | 3/2008 |
| WO | 2008091515 A2 | 7/2008 |
| WO | 2008/147964 A1 | 12/2008 |
| WO | 2008/150529 A1 | 12/2008 |
| WO | 2009024859 A2 | 2/2009 |
| WO | 2009033469 A1 | 3/2009 |
| WO | 2010121076 A2 | 10/2010 |
| WO | 2011025970 | 3/2011 |

OTHER PUBLICATIONS

Andersen, et al., "Transluminal implantation of artificial heart valves. Description of a new expandable aortic valve and initial results with implantationby catheter technique in closed chest pigs." European Heart Journal (1992), 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Serruys, P.W., et al., "Stenting of Coronary Arteries. Are we the Sorcerer's Apprentice?," European Heart Journal (1989) 10, 774-782, pp. 37-45, Jun. 13, 1989.
Kolata, Gina, "Device That Opens Clogged Arteries Gets a Failing Grade in a New Study," nytimes.com, http://www.nytimes.com/1991/01/03/health/device-that-opens-clogged-arteri- es-gets-a-faili . . . , Jul. 29, 2009, 2 pages.
Urban, M.D., Philip, "Coronary Artery Stenting," Editions Medecine et Hygiene, Geneve, 1991, pp. 5-47.
Al-Khaja, N., et al., "Eleven Years' Experience with Carpentier-Edwards Biological Valves in Relation to Survival and Complications," European Journal of Cardiothoracic Surgery 3:305-311, Jun. 30, 2009.
Wheatley, M.D., David J., "Valve Prostheses," Rob & Smith's Operative Surgery, Fourth Edition, pp. 415-424, Butterworths 1986.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Uchida, Barry T., et al., "Modifications of Gianturco Expandable Wire Stents," AJR:150, May 1988, Dec. 3, 1987, pp. 1185-1187.
Selby, M.D., J. Bayne, "Experience with New Retrieval Forceps for Foreign Body Removal in the Vascular, Urinary, and Biliary Systems," Radiology 1990; 176:535-538.
Inoune, M.D., Kanji, et al., "Clinical Application of Transvenous Mitral Commissurotomy by a New Balloon Catheter," The Journal of Thoracic and Cardiovascular Surgery 87:394-402, 1984.
Al Zaibag, Muayed, et al., "Percutaneous Balloon Valvotomy in Tricuspid Stenosis," British Heart Journal, Jan. 1987, vol. 57, No. 1, pp. 51-53.
Lawrence, Jr., M.D., David D., "Percutaneous Endovascular Graft: Experimental Evaluation," Radiology 1987, 163: 357-360.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Sigwart, Ulrich, "An Overview of Intravascular Stents: Old and New," Chapter 48, Textbook of Interventional Cardiology, 2.sup.nd Edition, W.B. Saunders Company, Philadelphia, PA, .Copyrgt. 1994, 1990, pp. 803-815.
Rosch, M.D., Josef, "The Birth, Early Years and Future of Interventional Radiology," J Vasc Interv Radiol 2003; 14:841-853.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Ross, F.R.C.S., D.N., "Aortic Valve Surgery," Guy's Hospital, London, pp. 192-197, approximately 1968.
Rashkind, M.D., William J., "Creationof an Atrial Septal Defect Withoput Thoracotomy," the Journal of the American Medical Association, vol. 196, No. 11, Jun. 13, 1966, pp. 173-174.
Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, p. 199-203.
Curriculum Vitae of Robert A. Ersek, M.D., FACS, Jul. 10, 2009, http://www.ersek.com/rae-cv.htm.
Partial Search Report from corresponding case No. PCT/US2009/048035 dated Feb. 26, 2010.
International Search Report, PCT/US2011/045072, dated Jun. 4, 2012.
Bailey, S. "Percutaneous Expandable Prosthetic Valves," Textbook of Interventional Cardiology vol. 2, 2nd Ed. pp. 1268-1276. 1994.

* cited by examiner

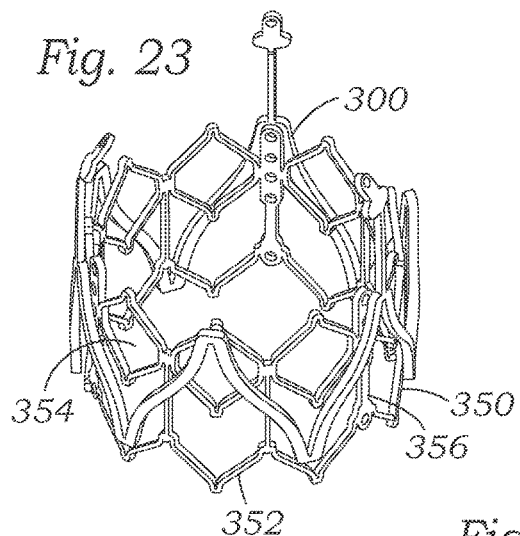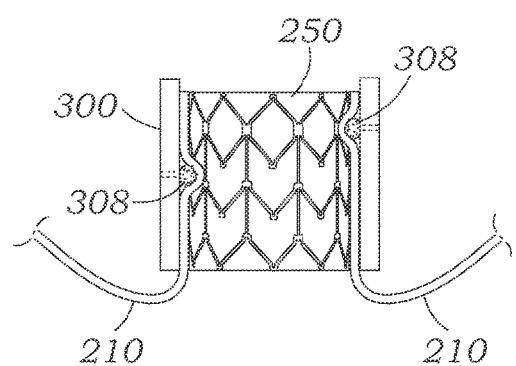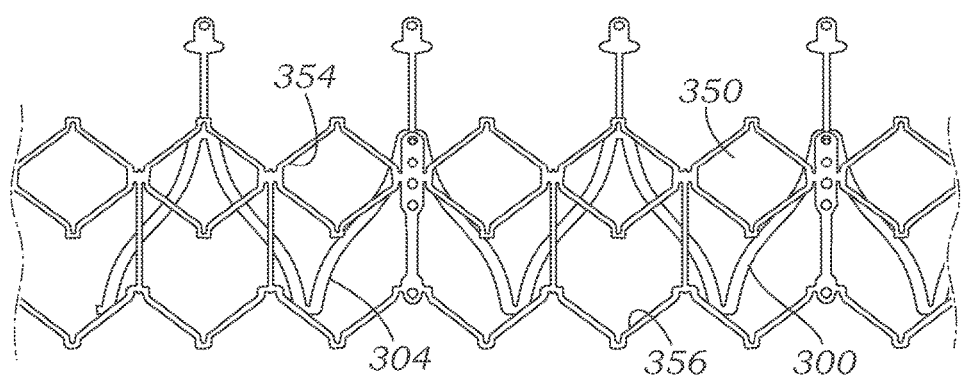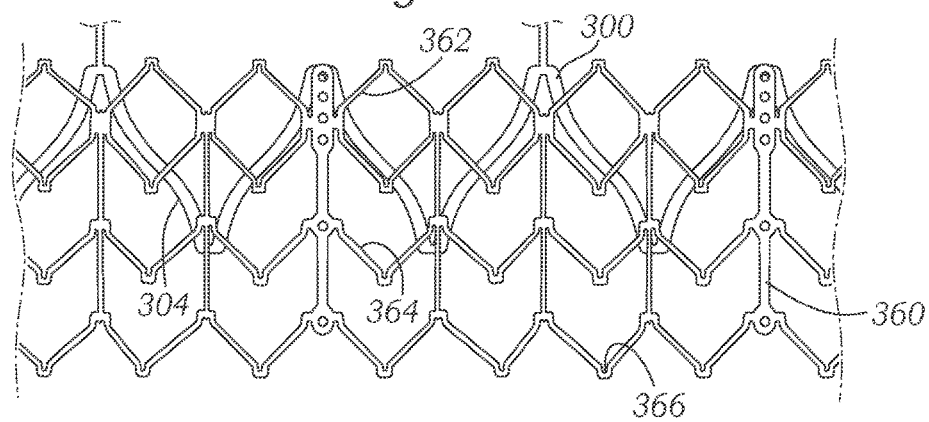

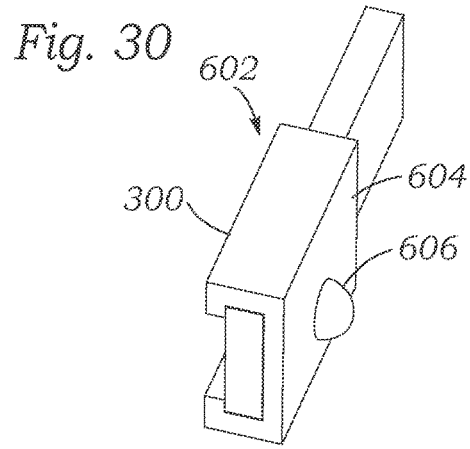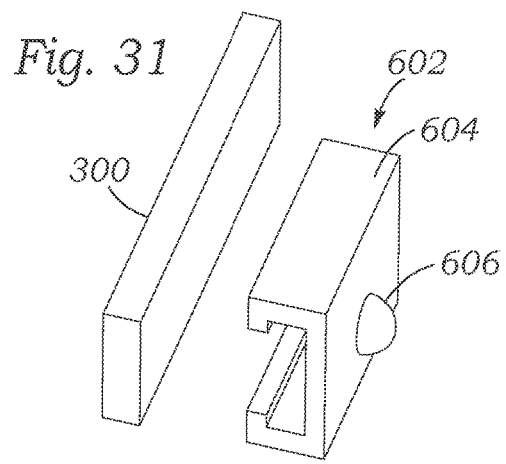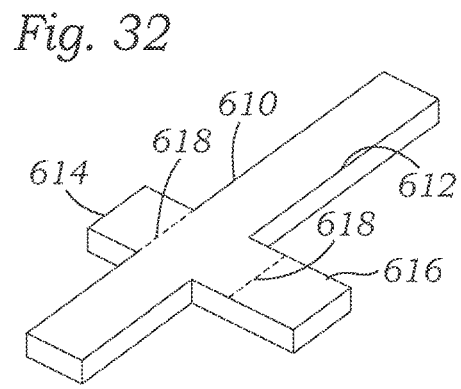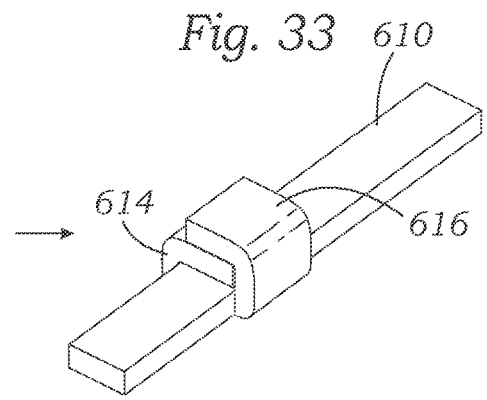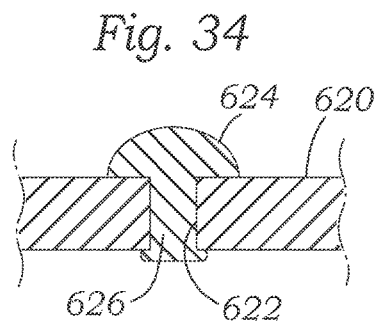

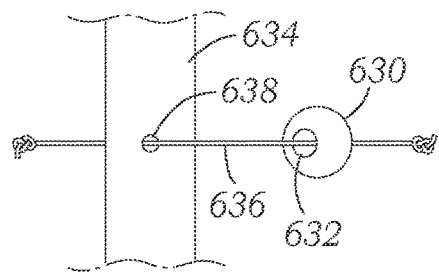
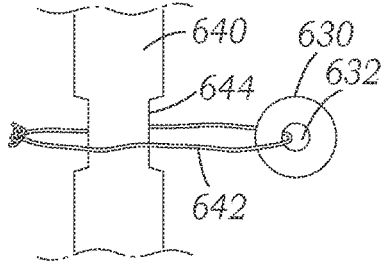
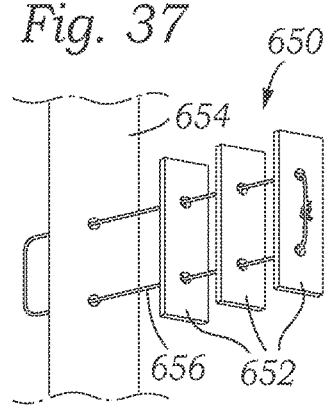
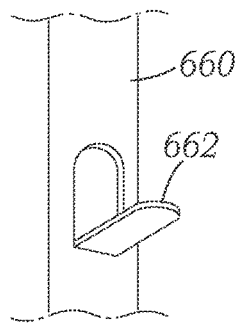
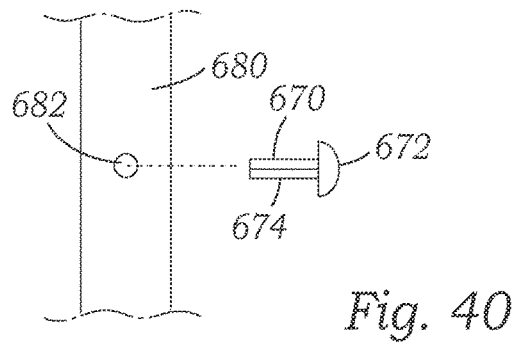

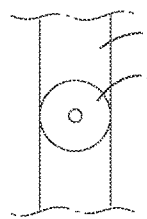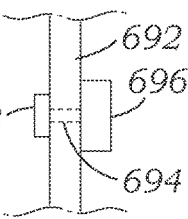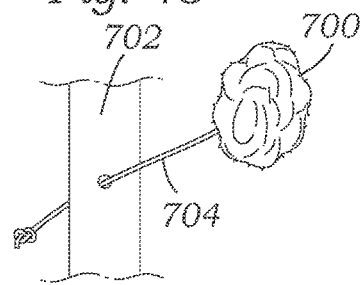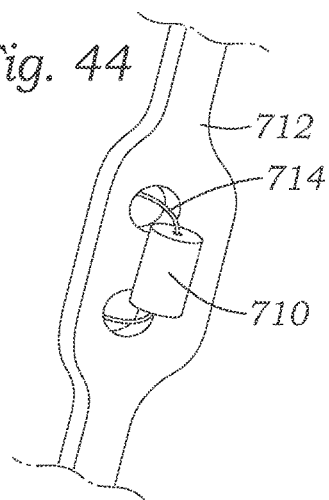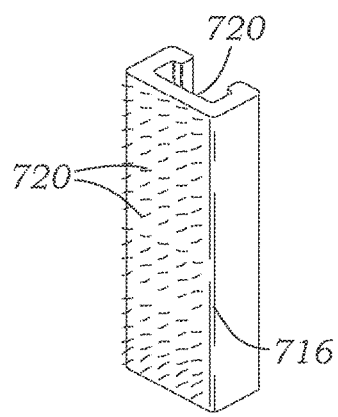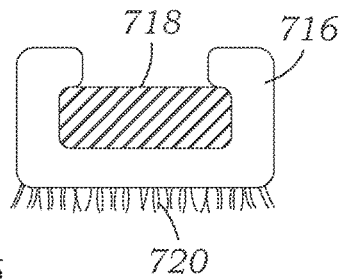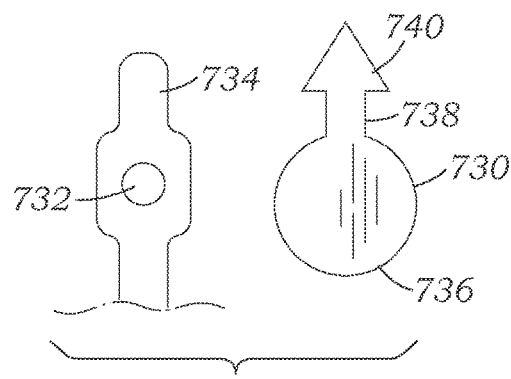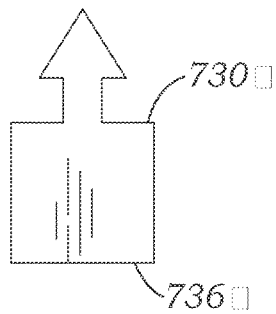

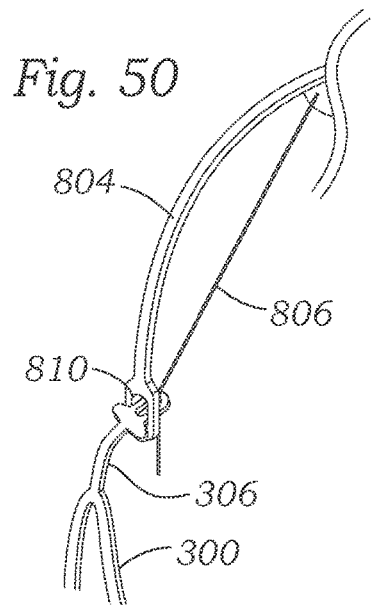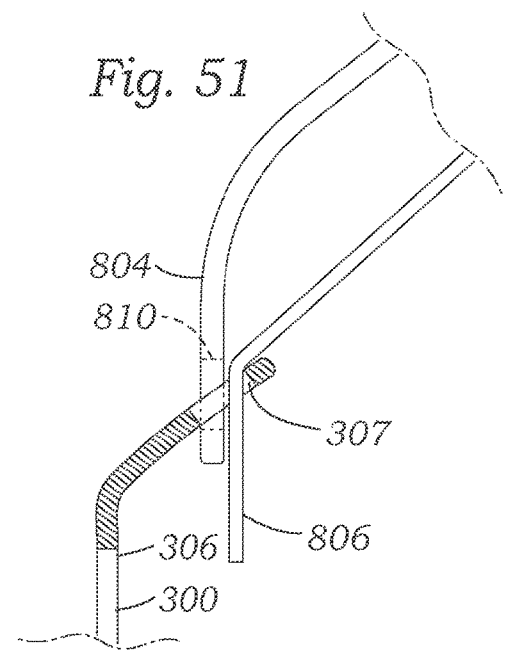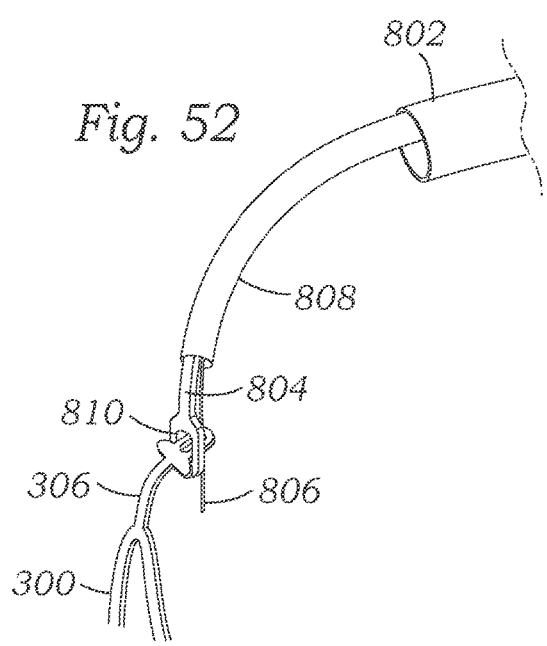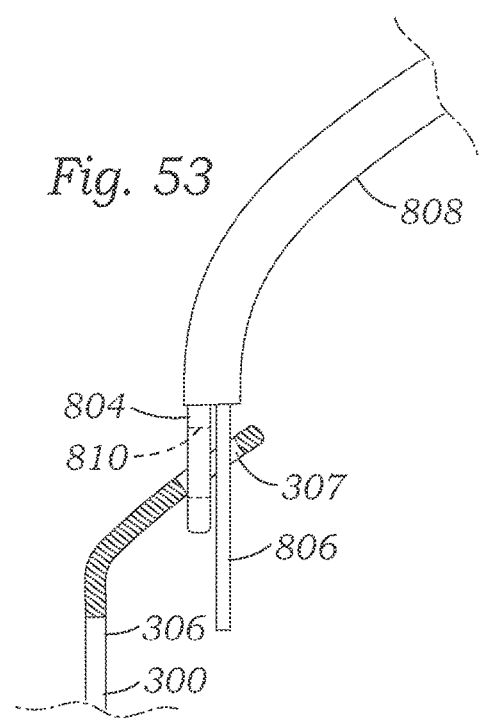

RETAINING MECHANISMS FOR PROSTHETIC HEART VALVES

CROSS-REFERENCE TO RELATED APPLICATION

The present application claims the benefit of U.S. Provisional Application No. 61/729,109, filed Nov. 21, 2012, which is incorporated herein by reference.

OTHER RELATED APPLICATIONS

The following applications, which are incorporated herein by reference, disclose retaining mechanisms for prosthetic heart valves and delivery systems for implanting such retaining mechanisms in the heart: U.S. Pat. No. 8,323,335, issued Dec. 4, 2012, and U.S. application Ser. No. 13/188,988, filed Jul. 22, 2011 (published as U.S. Patent Application Publication No. 2012/0022633 A1).

FIELD

This application relates to methods, systems, and apparatus for safely replacing native heart valves with prosthetic heart valves.

BACKGROUND

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to change over time, making it dangerous to install a prosthetic valve that is not reliably secured in the valve annulus. Mitral insufficiency (or mitral regurgitation) involves these same issues, but affects the mitral valve.

Self-expanding prosthetic valves are sometimes used for replacing defective native valves with non-calcified leaflets. Self-expanding prosthetic valves, however, suffer from a number of significant drawbacks. For example, once a self-expanding prosthetic valve is placed within the patient's defective heart valve (e.g., the aorta or mitral valve), it continues to exert an outward force on the valve annulus. This continuous, outward pressure can cause the valve annulus to dilate further, exacerbating the condition that the prosthetic valve was intended to treat. Additionally, when implanting a self-expanding valve, the outward biasing force of the valve's frame tends to cause the valve to be ejected very quickly from the distal end of a delivery sheath, making delivery of the valve very difficult and potentially dangerous to the patient.

The size of the prosthetic valve to be implanted into a patient can also be problematic when treating aortic or mitral insufficiency. Specifically, the size of a prosthetic valve used to treat aortic or mitral insufficiency is typically larger than a prosthetic valve used to treat aortic or mitral stenosis. This larger valve size makes the delivery procedure much more difficult and dangerous to the patient.

Accordingly, there exists a need for improved methods, systems, and apparatus for delivering expandable prosthetic heart valves (e.g., balloon-expandable prosthetic valves). Embodiments of the methods, systems, and apparatus desirably can be used to replace native heart valves that do not have calcified leaflets (e.g., aortic valves suffering from aortic insufficiency). Furthermore, embodiments of the methods, systems, and apparatus desirably enable precise and controlled delivery of the prosthetic valves.

SUMMARY

According to one representative embodiment, a method of treating aortic insufficiency comprises delivering a support structure to a position on or adjacent to the surface of the outflow side of a native heart valve of a patient. The support structure comprises an annular body defining an interior and at least one projection extending radially inwardly from the annular body. The method further includes positioning the support structure around the leaflets of the native heart valve such that the leaflets of the native heart valve are located within the interior of the annular body. An expandable prosthetic heart valve can be advanced into the native heart valve and into the interior of the annular body. The prosthetic heart valve can comprise a radially expandable annular frame defining a plurality of openings. The prosthetic heart valve can be expanded into contact with the leaflets of the native valve, thereby causing the leaflets of the native valve to be frictionally secured between an inner surface of the annular body and an outer surface of the prosthetic heart valve and causing the at least one projection and a portion of one of the leaflets contacted by the at least one projection to extend into one of said openings of the frame.

In another representative embodiment, an assembly for treating aortic insufficiency comprises a prosthetic heart valve and a separate support stent. The prosthetic heart valve is configured to be implanted within a native heart valve, and comprises a radially expandable annular frame defining a plurality of openings. The support stent is configured to be implanted around the leaflets of the native heart valve such that the native leaflets can be frictionally secured between the support stent and the prosthetic valve. The support stent comprises an annular metal frame that defines one or more peaks and one or more valleys along its circumference. The support stent frame is radially compressible into a compressed state and self-expandable into an uncompressed state and further comprises at least one projection comprising a non-metallic material. The at least one projection extends radially inwardly from the support stent frame and is configured to press a portion of one of the native leaflets into one of the openings of the frame of the prosthetic valve.

In another representative embodiment, a delivery apparatus for delivering a radially self-expandable prosthetic device to a native heart valve comprises a first elongated shaft having a distal end portion and a second elongated shaft extending over the first shaft. A plurality of attachment arms extend distally from the distal end portion of the first shaft, each attachment arm having an aperture configured to receive an end portion of a retaining arm of the prosthetic device. A plurality of release wires extend alongside the attachment arms and are configured to extend through corresponding openings in the end portions of the retaining arms when the end portions of the retaining arms are inserted through corresponding openings in the attachment arms so as to releasably secure the prosthetic device to the attachment arms. A plurality of sheaths extend distally from the distal end of the first shaft, each sheath extending co-axially over a respective pair of an attachment arm and a release wire so as to maintain the release wire in close proximity to the attachment arm.

In another representative embodiment, a delivery apparatus for delivering a radially self-expandable prosthetic device to a native heart valve comprises a first elongated shaft having a proximal end portion and a distal end portion. The distal end portion is configured to be releasably coupled to the prosthetic device during delivery of the prosthetic device into a patient. The apparatus further includes a second elongated shaft having a proximal end portion and a distal end portion. The second shaft extends over the first shaft, the distal end portion of the second shaft comprising a sheath configured to at least partially receive the prosthetic device in a radially compressed state. The second shaft is configured to be selectively bendable. A handle is coupled to the proximal end portions of the first and second shafts. The handle has an adjustment mechanism configured to adjust the curvature of the second shaft. The first shaft is allowed to move in a proximal direction relative to the second shaft and the handle when the second shaft foreshortens as a result of the adjustment mechanism being actuated to increase the curvature of the second shaft.

In another representative embodiment, a delivery apparatus for delivering a radially self-expandable prosthetic device to a native heart valve comprises a first elongated shaft having a proximal end portion and a distal end portion. The distal end portion is configured to be releasably coupled to the prosthetic device during delivery of the prosthetic device into a patient. The delivery apparatus further comprises a second elongated shaft having a proximal end portion and a distal end portion, the second shaft extending over the first shaft. The distal end portion of the second shaft comprises a sheath configured to at least partially receive the prosthetic device in a radially compressed state. A handle is coupled to the proximal end portions of the first and second shafts. The handle comprises a rotatable knob operatively connected to the first shaft and configured to effect axial movement of the first shaft relative to the second shaft to deploy the prosthetic device from the sheath of the second shaft. The handle further comprising a spring configured to provide resistance against rotation of the knob. In particular embodiments, the resistance of the spring is greater against rotation of the knob in a first direction than it is against rotation of the knob in a second direction, opposite the first direction.

The foregoing and other objects, features, and advantages of the invention will become more apparent from the following detailed description, which proceeds with reference to the accompanying figures.

BRIEF DESCRIPTION OF THE DRAWINGS

FIG. 3 shows the delivery system before the support structure is deployed, and FIG. 4 shows the delivery system after the support structure is deployed.

FIG. 23 is a perspective view of the support stent of FIGS. 14-15 mounted around the frame of a prosthetic valve.

FIG. 24 shows a prosthetic valve implanted with a native aortic valve and the support stent of FIGS. 14-15 implanted around the native leaflets of the aortic valve such that the native leaflets are pinched between the prosthetic valve and the support stent.

FIG. 25 is a flattened view of the support stent and the prosthetic valve frame shown in FIG. 23.

FIG. 26 is a flattened view of the support stent of FIG. 25 and another example of a prosthetic valve frame.

FIGS. 30-48 show different techniques and mechanisms for forming a projection on a support stent.

FIGS. 50-53 are enlarged views showing the releasable connection between a retaining arm of a support stent and a pair of an attachment arm and a release wire of the delivery apparatus of FIG. 49.

DETAILED DESCRIPTION

General Considerations

Figure 1:
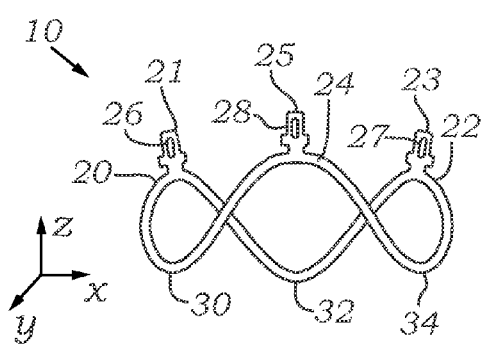
FIG. 1 is a perspective view of an exemplary embodiment of a support structure according to the disclosed technology.

Disclosed below are representative embodiments of a support structure (sometimes referred to as a "support stent," "support frame," "support band," or "support loop") that can be used to secure a prosthetic heart valve within a native heart valve. For illustrative purposes, embodiments of the support structure are described as being used to secure a transcatheter heart valve ("THV") in the aortic valve or the mitral valve of a heart. It should be understood that the disclosed support structure and THV can be configured for use with any other heart valve as well. Also disclosed herein are exemplary methods and systems for deploying the support structure and corresponding THV. Although the exemplary methods and systems are mainly described in connection with replacing an aortic or mitral valve, it should be understood that the disclosed methods and systems can be adapted to deliver a support structure and THV to any heart valve.

For illustrative purposes, certain embodiments of the support structure are described as being used in connection with embodiments of the balloon-expandable THV described in U.S. Patent Application Publication No. 2007/0112422 A1 (U.S. application Ser. No. 11/280,063), which is hereby expressly incorporated herein by reference. It should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure. U.S. Pat. No. 6,730,118 is hereby expressly incorporated herein by reference.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "coupled" generally means physically coupled or linked and does not exclude the presence of intermediate elements between the coupled items absent specific contrary language.

Exemplary Embodiments for Replacing Aortic Valves

FIG. 1 is a perspective view showing an exemplary embodiment of a support stent or frame 10. Support stent 10 has a generally annular or toroidal body formed from a suitable shape-memory metal or alloy, such as spring steel, Co—Cr—Ni alloy (Elgiloy®), or nitinol. Desirably, the material from which the support stent 10 is fabricated allows the support stent to automatically expand to its functional size and shape when deployed but also allows the support stent to be radially compressed to a smaller profile for delivery through the patient's vasculature. In other embodiments, however, the stent is not self-expanding. In these embodiments, and as more fully explained below, other mechanisms for expanding the stent can be used (e.g., a balloon catheter).

In the illustrated embodiment, the projection of the support stent 10 onto an x-y plane has a generally annular or toroidal shape. The illustrated support stent 10 further defines a number of peaks and valleys (or crests and troughs) along its circumference. For example, the support stent 10 is sinusoidally shaped in the z direction. In other embodiments, the support stent 10 is shaped differently in the z direction (e.g., sawtooth-shaped, ringlet-shaped, square-wave shaped, or otherwise shaped to include peaks and valleys).

The illustrated support stent 10 includes three peaks 20, 22, 24 and three valleys 30, 32, 34. In the illustrated embodiment, the peaks 20, 22, 24 are positioned above the valleys 30, 32, 34 in the z-direction. In some embodiments, the peaks have greater radii than the valleys 30, 32, 34, or vice versa. For instance, in some embodiments, the projection of the support stent 10 onto an x-y plane forms a closed shape having a variable radius (e.g., a starfish shape).

The size of the support stent 10 can vary from implementation to implementation. In particular embodiments, the support stent 10 is sized such that the support stent can be positioned within the aorta of a patient at a location adjacent to the aortic valve, thereby circumscribing the aortic valve. Furthermore, in order to frictionally secure a prosthetic heart valve in its interior, certain embodiments of the support stent 10 have a diameter that is equal to or smaller than the diameter of the prosthetic heart valve when fully expanded. In particular embodiments, for instance, the support stent can have an inner or outer diameter between about 10 mm and about 50 mm (e.g., between about 17 mm and about 28 mm) and a height between about 5 mm and about 35 mm (e.g., between about 8 mm and about 18 mm). Furthermore, the thickness of the annular body of the support stent 10 may vary from embodiment to embodiment, but in certain embodiments is between about 0.3 mm and about 1.2 mm.

Figure 2:
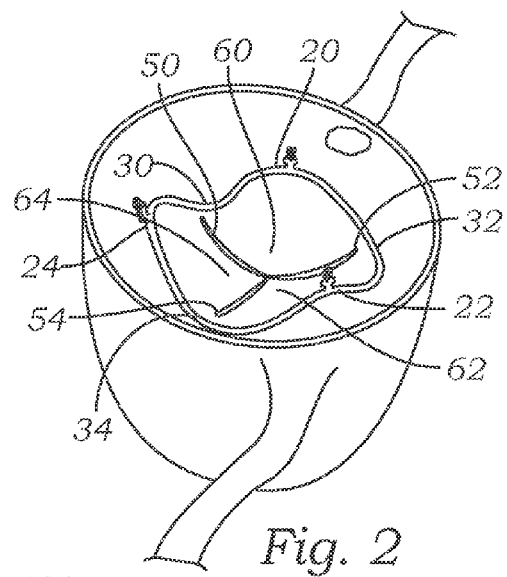
FIG. 2 is a cross-sectional view of a native aortic valve with the support structure of FIG. 1 positioned therein.

FIG. 2 is a perspective view of the exemplary support stent 10 positioned on the surface of an outflow side of a native aortic valve and further illustrates the shape of the support stent. In particular, it can be seen from FIG. 2 that the valleys 30, 32, 34 of the support stent 10 are shaped so that they can be placed adjacent to commissures 50, 52, 54 of the native leaflets 60, 62, 64 of the aortic valve. Furthermore, in the illustrated embodiment, the peaks 20, 22, 24 are shaped so that they generally approximate or mirror the size and shape of the leaflets 60, 62, 64 but are slightly smaller and lower than the height of the leaflets 60, 62, 64 at their tips when the aortic valve is fully opened. In other embodiments, the peaks 20, 22, 24 are oriented so that they are adjacent to the commissures 50, 52, 54 of the native leaflets 60, 62, 64 and the valleys are opposite the apexes of the leaflets 60, 62, 64. The support stent 10 can be positioned in any other orientation within the aortic valve as well.

It should be understood that the shape of the support stent or frame 10 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIGS. 1 and 2 is formed from a single annular member (or strut), the support stent can comprise multiple annular elements that interlock or are otherwise connected to one another (e.g., via multiple longitudinal members).

Returning to FIG. 1, the illustrated support stent 10 also include retaining arms 21, 23, 25 that can be used to help position and deploy the support stent 10 into its proper location relative to the native aortic valve. The retaining arms 21, 23, 25 can have respective apertures 26, 27, 28. An exemplary deployment system and procedure for deploying the support stent 10 using the retaining arms 21, 23, 25 are described in more detail below. The support stent 10 can also have one or more barbs located on its surface. Such barbs allow the support stent 10 to be more securely affixed to the tissue surrounding the stent or the leaflets of the aorta.

Figure 3:
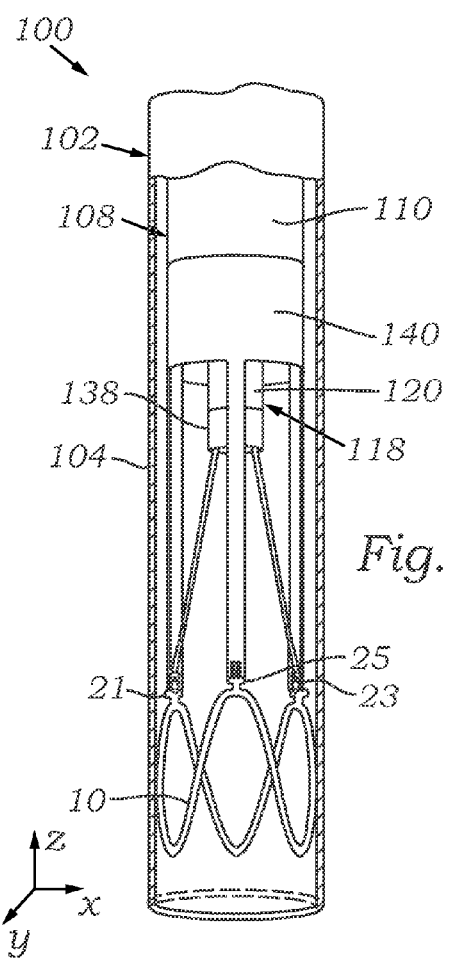
FIGS. 3 and 4 are perspective views of an exemplary delivery system for the support structure of FIG. 1. In particular.
Figure 4:
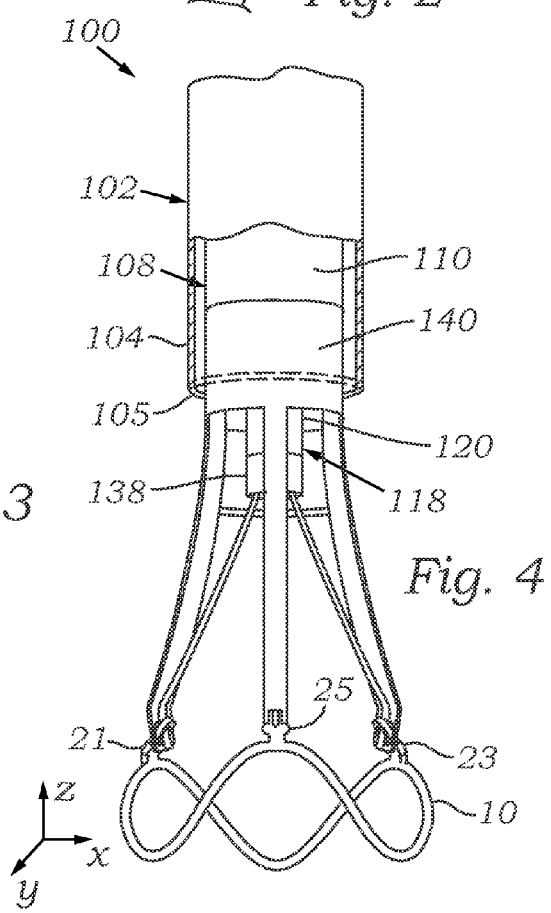

FIGS. 3 and 4 are side views of the distal end portion of an exemplary delivery apparatus 100 for delivering the support stent 10 to its location adjacent the native aortic valve through a patient's vasculature. In particular, FIG. 3 shows the delivery apparatus when the support stent 10 is in a compressed, pre-deployed state, whereas FIG. 4 shows the delivery apparatus when the support stent 10 is in a decompressed, deployed state. The delivery apparatus 100 comprises a guide catheter 102 having an elongated shaft 104, whose distal end 105 is open in the illustrated embodiment. In other embodiments, the distal end 105 of the guide catheter 102 can be tapered into a conical shape comprising multiple "flaps" forming a protective nose cone that can be urged apart when the support stent 10 and any interior catheters are advanced therethrough. Furthermore, for illustrative purposes, the guide catheter 102 is shown as being partially cut away, thus revealing its interior.

A proximal end (not shown) of the guide catheter 102 is connected to a handle of the delivery apparatus 100. During delivery of a support stent, the handle can be used by a surgeon to advance and retract the delivery apparatus through the patient's vasculature. In a particular use, the delivery apparatus 100 is advanced through the aortic arch of a patient's heart in the retrograde direction after having been percutaneously inserted through the femoral artery. The guide catheter can be configured to be selectively steerable or bendable to facilitate advancement of the delivery system 100 through the patient's vasculature. An exemplary steerable guide catheter as can be used in embodiments of the disclosed technology is described in detail in U.S. Patent Application Publication No. 2007/0005131 A1 (U.S. patent application Ser. No. 11/152,288), which is hereby expressly incorporated herein by reference.

The delivery apparatus 100 also includes a stent delivery catheter 108 positioned in the interior of the guide catheter 102. The stent delivery catheter 108 has an elongated shaft 110 and an outer fork 140 connected to a distal end portion of the shaft 110. The shaft 110 of the stent delivery catheter 108 can be configured to be moveable axially relative to the shaft 104 of the guide catheter 102. Furthermore, the shaft 110 of the stent delivery catheter 108 can be sized so that its exterior wall is adjacent to or in contact with the inner wall of the shaft 104 of the guide catheter 102.

The delivery apparatus 100 can also include an inner catheter 118 positioned in the interior of the stent deliver catheter 108. The inner catheter 118 can have an elongated shaft 120 and an inner fork 138 secured to the distal end portion of the shaft 120. The shaft 120 of the inner catheter 118 can be configured to be moveable axially relative to the shaft 104 of the guide catheter 102 and relative to the shaft 110 of the stent delivery catheter 108. Furthermore, the shaft 120 of the inner catheter 118 can be sized so that its exterior wall is adjacent to or in contact with the inner wall of the shaft 110 of the stent delivery catheter 108. A guide wire (not shown) can be inserted into the interior of the inner catheter 118. The guide wire can be used, for example, to help ensure proper advancement of the guide catheter 102 and its interior catheters through the vasculature of a patient.

Figure 5:
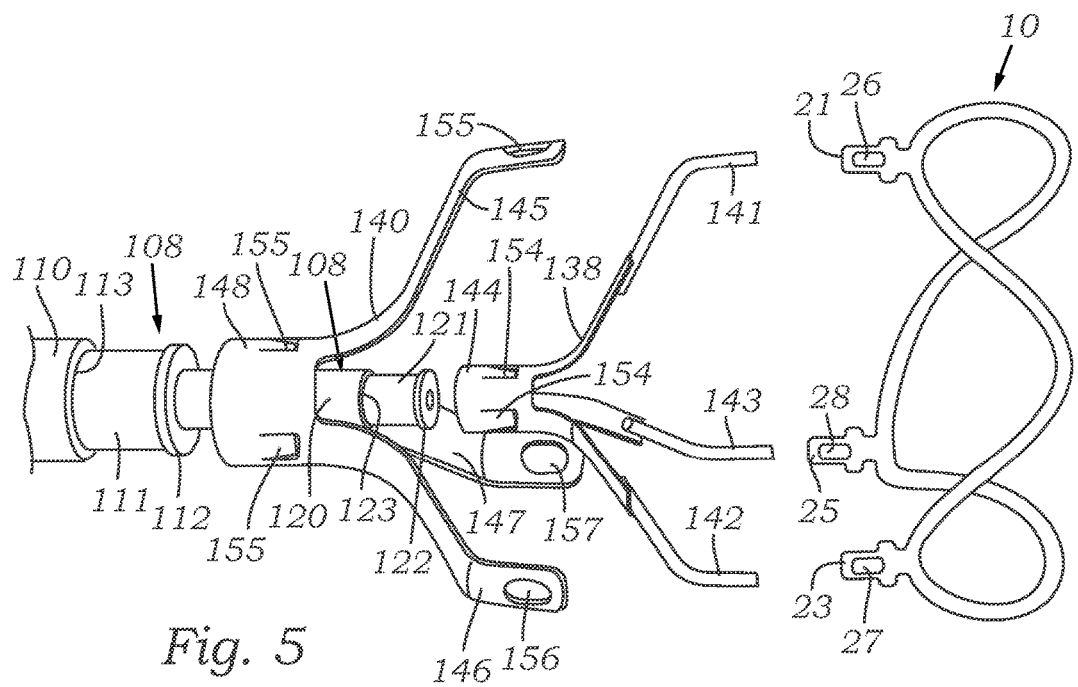
FIG. 5 is an exploded view of the components of the exemplary delivery system shown in FIGS. 3 and 4.

As best shown in FIG. 5, a stent retaining mechanism is formed from the inner fork 138 attached to the distal end portion of the shaft 120 of the inner catheter 118 and the outer fork 140 attached to the distal end portion of the shaft 110 of the stent delivery catheter 108. The inner fork 138 includes a plurality of flexible inner prongs 141, 142, 143 (three in the illustrated embodiment) at its distal end corresponding to the retaining arms 21, 23, 25 of the support stent 10, and a head portion 144 at its proximal end. The outer fork 140 includes a plurality of flexible outer prongs 145, 146, 147 (three in the illustrated embodiment) at its distal end corresponding to the retaining arms 21, 23, 25 of the stent 10, and a head portion 148 at its proximal end. The distal end portions of the outer prongs 145, 146, 147 are formed with respective apertures 155, 156, 157 sized to receive the retaining arms 21, 23, 25.

Figure 6:
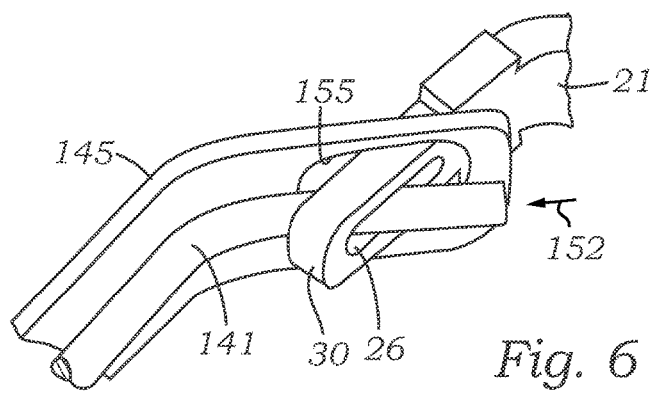
FIG. 6 is a zoomed-in perspective view showing the mechanism for releasably connecting the support structure to the exemplary delivery system of FIGS. 3 and 4.

FIG. 6 is a zoomed-in view of one of the retaining arms 21, 23, 25 as it interfaces with corresponding prongs of the outer fork 140 and the inner fork 138. In this example, retaining arm 21 is shown, though it should be understood that the retaining mechanism is similarly formed for the retaining arms 23, 25. The distal end portion of the outer prong 145 is formed with the aperture 155. When assembled, the retaining arm 21 of the stent is inserted through the aperture 155 of the prong 145 of the outer fork and the prong 141 of the inner fork is inserted through the aperture 26 of the retaining arm 21 so as to retain the retaining arm 21 in the aperture 155.

Retracting the inner prong 141 proximally (in the direction of arrow 152) to remove the prong from the aperture 26 allows the retaining arm 21 to be removed from the aperture 155, effectively releasing the retaining arm from the retaining mechanism. For instance, the outer prong 145 and the retaining arm 21 can be formed such that when the inner prong 141 is withdrawn from the aperture 26, the outer prong 145 flexes radially inward (downward in FIG. 7) and/or the retaining arm 21 of the support stent flexes radially outward (upward in FIG. 7), thereby causing the retaining arm 21 to be removed from the aperture 155. In this manner, the retaining mechanism formed by the inner fork 138 and the outer fork 140 create a releasable connection with the support stent 10 that is secure enough to retain the support stent to the stent delivery catheter 108 and to allow the user to adjust the position of the support stent after it is deployed. When the support stent 10 is positioned at the desired location adjacent to the leaflets of the aortic valve, the connection between the support stent and the retaining mechanism can be released by retracting the inner fork 138 relative to the outer fork 140, as further described below. In other embodiments, the functions of the inner fork and the outer fork can be reversed. For example, the prongs of the inner fork can be formed with apertures sized to receive the corresponding retaining arms of the support stent and the prongs of the outer fork can be inserted through the apertures of the retaining arms when the retaining arms are placed through the apertures of the prongs of the inner fork.

As best shown in the exploded view in FIG. 5, the head portion 144 of the inner fork can be connected to the distal end portion of the shaft 120 of the inner catheter 118. In the illustrated embodiment, for example, the head portion 144 of the inner fork is formed with a plurality of angularly spaced, inwardly biased retaining flanges 154. An end piece of the shaft 120 can be formed as a cylindrical shaft having an annular groove 121. On the distal side of the annular groove 121, the shaft 120 can have a collar 122 with an outer diameter that is slightly greater than the diameter defined by the inner free ends of the flanges 154. Thus, the inner fork 138 can be secured to the end piece by inserting head portion 144 of the inner fork onto the end piece of the shaft 120 until the flanges 154 flex inwardly into the annular groove 121 adjacent the collar 122, thereby forming a snap-fit connection between the head portion 144 and the shaft 120. The head portion 144 can have a proximal end that engages an annular shoulder 123 of the shaft 120 that is slightly larger in diameter so as to prevent the head portion from sliding longitudinally along the shaft 120 in the proximal direction.

The head portion 148 of the outer fork can be secured to a distal end portion of the shaft 110 of the stent delivery catheter 108 in a similar manner. As shown in FIG. 5, the head portion 148 can be formed with a plurality of angularly spaced, inwardly biased retaining flanges 155. An end piece of the shaft 110 can be formed as a cylindrical shaft having an annular groove 111. On the distal side of the annular groove 111, the shaft 110 can have a collar 112 with an outer diameter that is slightly greater than the diameter defined by the free ends of the flanges 155. Thus, the outer fork 140 can be secured to the end piece of the shaft 110 by inserting the shaft 110 onto the head portion 148 until the flanges flex inwardly into the groove 111, thereby forming a snap-fit connection between the head portion 148 and the shaft 110. The head portion 148 can have a proximal end that engages an annular shoulder 123 of the shaft 110 that is slightly larger so as to prevent the head portion from sliding longitudinally along the shaft 110 in the proximal direction.

In FIG. 3, the support stent 10 is shown in a radially compressed state in the interior of the elongated shaft 104 of the guide catheter 102. In the radially compressed state, the distance along the z-axis between a peak and an adjacent valley of the support stent is greater than the distance along the z-axis between the peak and the adjacent valley when the support stent is in it uncompressed state. The distal end portion of the shaft 104 can also be referred to as a delivery sheath for the stent 10. In this undeployed and compressed state, the prongs of the outer fork 140 and the inner fork 138 of the stent delivery catheter 108 and the inner catheter 118 engage the retaining arms 21, 23, 25 of the support stent 10 in the manner described above with respect to FIGS. 5 and 6. To deploy the support stent 10 in the illustrated embodiment (to advance the stent from the delivery system), the stent delivery catheter 108 and the inner catheter 118 are advanced toward the distal end 105 of the guide catheter 102 using one or more control handles or mechanisms (not shown) located at the proximal end of the guide catheter 102. This action causes the support stent 10 to be advanced outwardly through the distal end 105 of the guide catheter 102 and expand into its relaxed, uncompressed state (shown, for example, in FIGS. 1 and 2).

FIG. 4 is a perspective view showing the support stent 10 after it has been advanced from the distal end of the guide catheter 102. As seen in FIG. 4, the support stent 10 now assumes its relaxed, uncompressed shape but remains connected to the outer fork 140 and the inner fork 138 at its retaining arms 21, 23, 25. In this configuration, the support stent 10 can be rotated (in the clockwise or counter-clockwise directions) or repositioned (in the proximal and distal directions and/or to a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 100 via the retaining arms 21, 23, 25. As more fully illustrated below in FIGS. 7-12, a prosthetic valve (e.g., a THV) can be delivered to the aortic valve through a transapical approach (e.g., through the apex of the heart and through the left ventricle) and deployed within the native valve such that the prosthetic valve is secured in place by frictional engagement between the support stent, the native leaflets, and the prosthetic valve.

In particular embodiments, the support stent 10 is shaped so that the THV can be positioned in the interior of the support stent along with the native leaflets of the aortic valve. More specifically, the support stent 10 can be shaped such that the native leaflets become trapped or pinched between the support stent 10 and the exterior of the THV when the THV is installed. For instance, the diameter of the support stent 10 can be equal to or smaller than the maximum diameter of the THV when fully expanded, thus causing the THV to be frictionally fit to the leaflets of the aortic valve and the support stent 10. This friction fit creates a solid foundation for the THV that is independent of the state or condition of the leaflets in the aortic valve. For example, THVs are most commonly used for treating aortic stenosis, a condition in which the leaflets of the aortic valve become hardened with calcium. The hardened leaflets typically provide a good support structure for anchoring the THV within the aortic annulus. Other conditions may exist, however, in which it is desirable to implant a THV into the aortic valve and which do not result in a hardening of the leaflets of the aortic valve. For instance, the support stent 10 can be used as a foundation for a THV when treating patients with aortic insufficiency. Aortic insufficiency results when the aortic annulus dilates such that the aortic valve does not close tightly. With this condition, the aortic annulus is larger than normal and would otherwise require a large THV. Using a support stent or frame (such as the support stent or frame 10), however, a smaller THV can be used, thereby making the THV delivery process easier and safer. Furthermore, the use of a support stent protects against displacement of the THV if there is any further dilation of the aortic valve.

A support stent can be used to secure a THV in any situation in which the aorta or aortic valve may not be in condition to help support the THV and is not limited to cases of aortic insufficiency. For example, a support stent 10 can be used in cases in which the aortic annulus is too dilated or in which the leaflets of the aorta are too weak or soft. The support stent can be used to create an anchor for the THV, for instance, in cases in which the native leaflet tissue is too soft because of excess collagen in the aorta.

Figure 7:
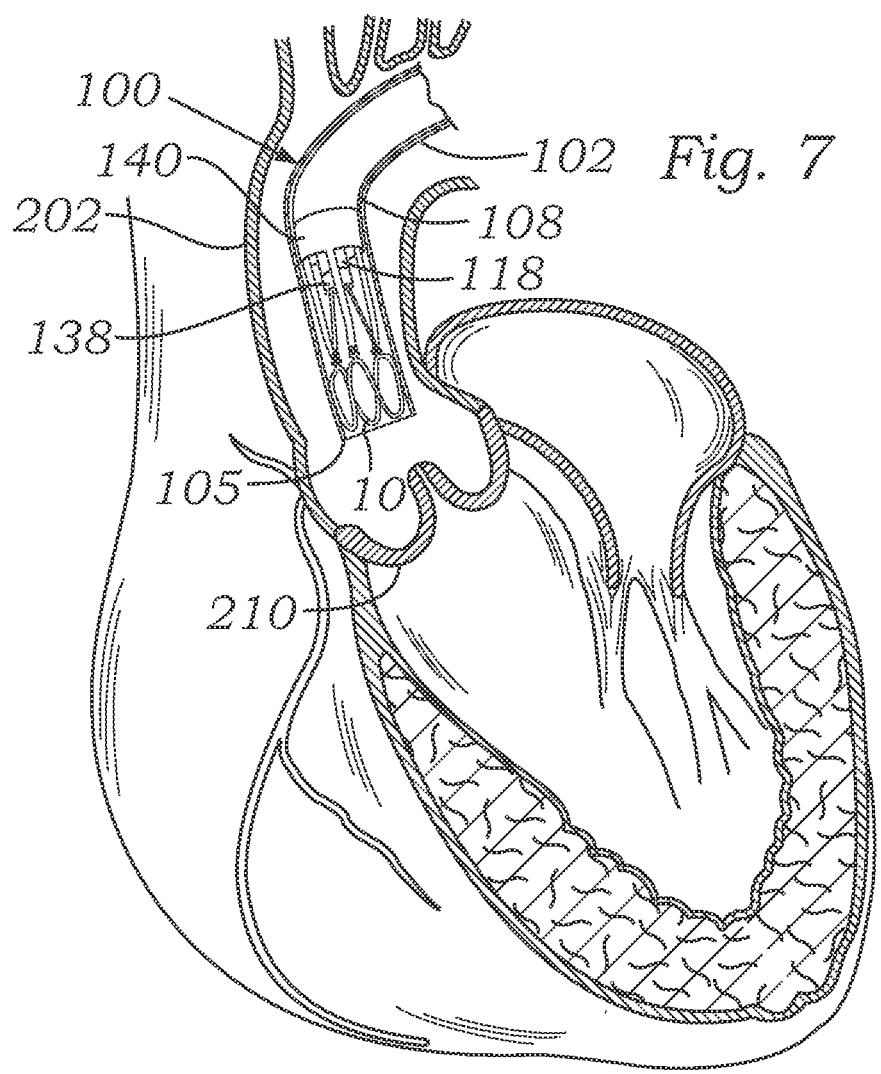
FIGS. 7 and 8 are cross-sectional views of a patient's heart illustrating how the delivery system of FIGS. 3 and 4 can operate to deploy the support structure of FIG. 1 to a desired position on the patient's aortic valve.
Figure 8:
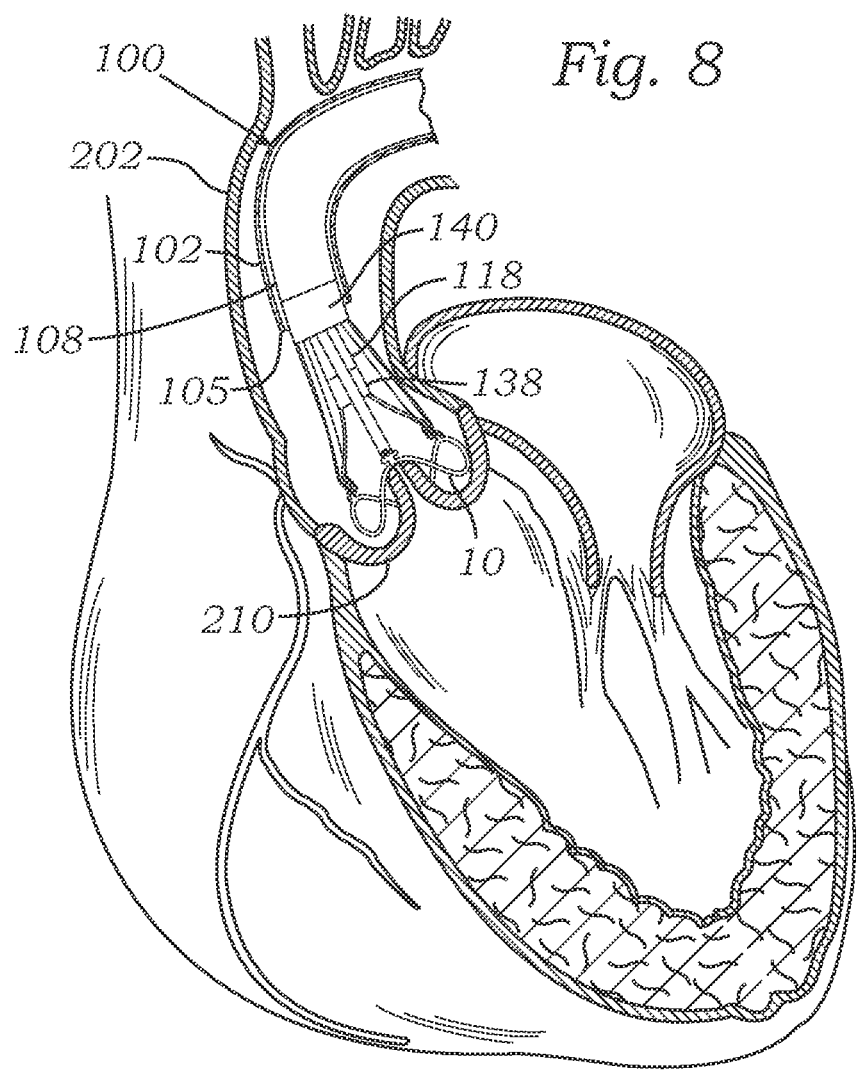

FIGS. 7-13 illustrate one exemplary procedure for deploying the support stent and securing a THV to the support stent. In particular, FIGS. 7-8 are cross-sectional views through the left side of a patient's heart showing the acts performed in delivering the support stent 10 through the aortic arch to the aortic valve. FIGS. 9-13 are cross-sectional views through the left side of a patient's heart showing the acts performed in deploying a THV 250 and having it engage the support stent 10. In order to better illustrate the components of the delivery system 100, the guide catheter 102 is shown partially cut away in FIGS. 7-13. For the sake of brevity, certain details concerning the delivery system of the THV 250 are omitted. Additional details and alternative embodiments of the delivery system for the THV 250 that may be used with the support stent described herein are discussed in U.S. Patent Application Publication No. 2007/0112422 A1 (U.S. patent application Ser. No. 11/280,063), which is hereby expressly incorporated herein by reference.

FIG. 7 shows the guide catheter 102 of the delivery system 100 as it is advanced through the aortic arch 202 into a position near the surface of the outflow side of the aortic valve 210. The delivery system 100 can be inserted through the femoral artery of the patient and advanced into the aorta in the retrograde direction. FIG. 7 also shows the stent delivery catheter 108, the inner catheter 118, and the support stent 10. In FIG. 7, the support stent 10 is in its radially compressed, pre-deployment state. Also seen in FIG. 7 are the outer fork 140 and the inner fork 138, which couple the radially compressed support stent 10 to the distal ends of the stent delivery catheter 108 and the inner catheter 118, respectively.

FIG. 8 shows the support stent 10 after it has been advanced through the distal end of the guide catheter 102 and assumes its final, uncompressed shape in a position above and adjacent to the aortic valve 210. The support stent 10 can also be placed directly on the surface of the outflow side of the aortic valve. FIG. 8 shows that the stent delivery catheter 108 and the inner catheter 118 have been advanced though the distal end of the guide catheter 102, thereby pushing the support stent 10 out of the guide catheter and allowing it to expand into its natural shape. In particular embodiments, the support stent 10 is rotated and positioned as necessary so that the support stent generally circumscribes the aortic valve and so that the peaks of the support stent are aligned with the tips of the natural leaflets of the aortic valve 210. Therefore, when the THV is inserted and expanded within the aortic valve 210, the leaflets of the aortic valve will engage at least the majority of the surface in the interior of the support stent 10. This alignment will create an overall tighter fit between the support stent 10 and the THV. In other embodiments, the support stent 10 is rotated and positioned as necessary so that the peaks of the support stent 10 are aligned with the commissures or other portions of the aortic valve. The position of the guide catheter 102 and the support stent 10 relative to the aortic valve 210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 8 are the prongs of the outer fork 140 and the prongs of the inner fork 138. In the exemplary procedure, the prongs of the outer fork 140 and the inner fork 138 remain secured to the support stent 10 until the THV is deployed and frictionally engaged to the support stent. The inner and outer forks desirably form a connection between the stent 10 and the delivery system that is secure and rigid enough to allow the surgeon to hold the stent 10 at the desired implanted position against the flow of blood while the THV is being implanted.

In FIG. 8, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 100. For example, the support stent can be disposed around a balloon of a balloon catheter in a compressed state. The balloon catheter can have a shaft that is interior to the inner catheter 118. Because the stent 10 is not self-expanding, the distal end portion of the guide catheter 102 need not extend over the compressed support stent. During delivery of the support stent, the support stent, balloon catheter, inner catheter 118, and stent delivery catheter 108 can be advanced from the distal end of the guide catheter 102. The balloon portion of the balloon catheter can be inflated, causing the support stent to expand. The balloon portion can subsequently be deflated and the balloon catheter withdrawn into the delivery system 100 to remove the balloon from the interior of the support stent while the support stent remains connected to the inner catheter for positioning of the support stent. The delivery of the support stent otherwise proceeds as in the illustrated embodiment using the self-expanding support stent 10.

Figure 9:
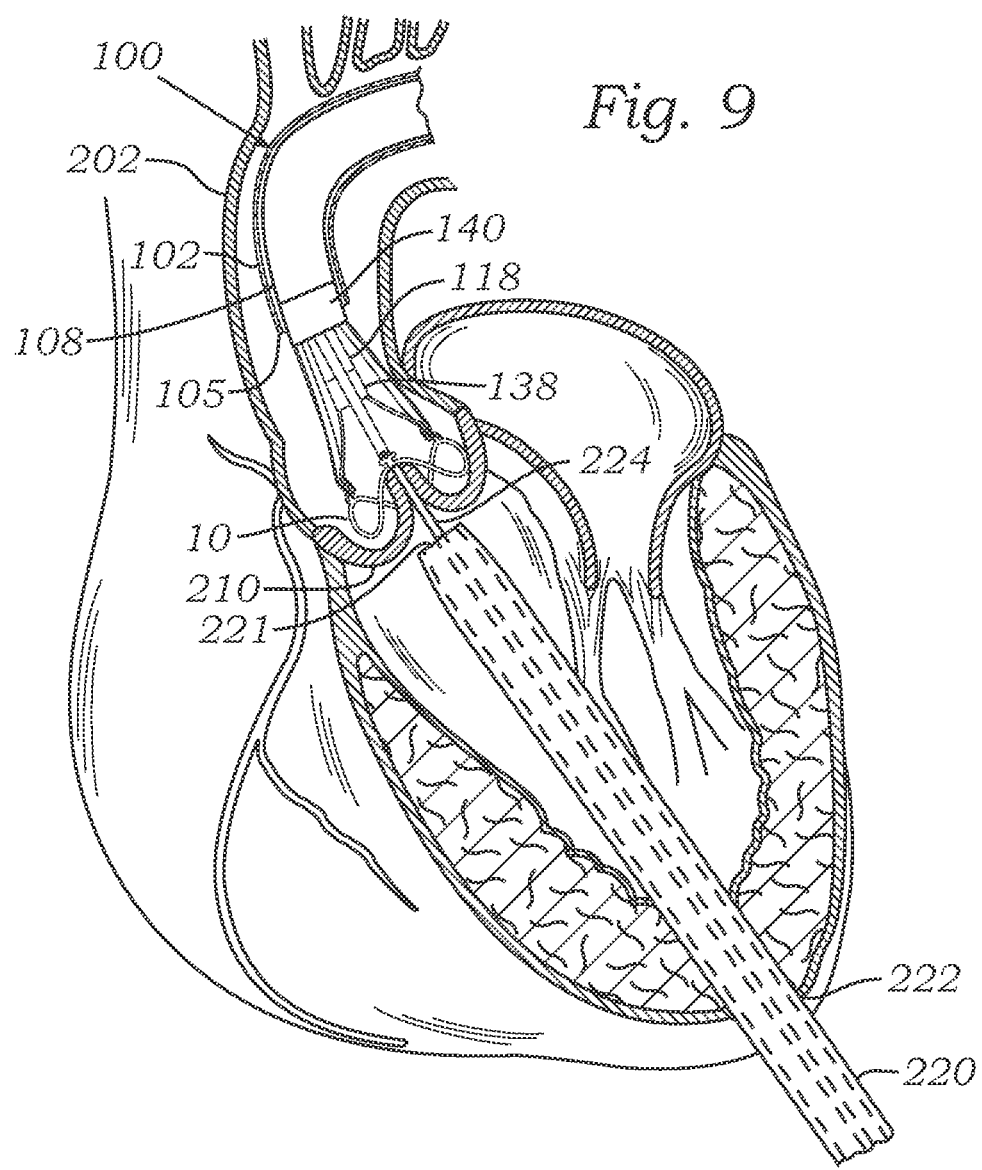
FIGS. 9-13 are cross-sectional views of a patient's heart illustrating how an exemplary transcatheter heart valve ("THV") can be deployed to the patient's aortic valve and frictionally secured to the native leaflets using the support structure of FIG. 1.

FIG. 9 shows an introducer sheath 220 passing into the left ventricle through a puncture 222 and over a guidewire 224 that extends upward through the aortic valve 210. The surgeon locates a distal tip 221 of the introducer sheath 220 just to the inflow side of the aortic valve 210. The position of the introducer sheath 220 relative to the aortic valve 210, as well as the position of other elements of the system, can be monitored using radiopaque markers and fluoroscopy, or using other imaging systems.

Figure 10:
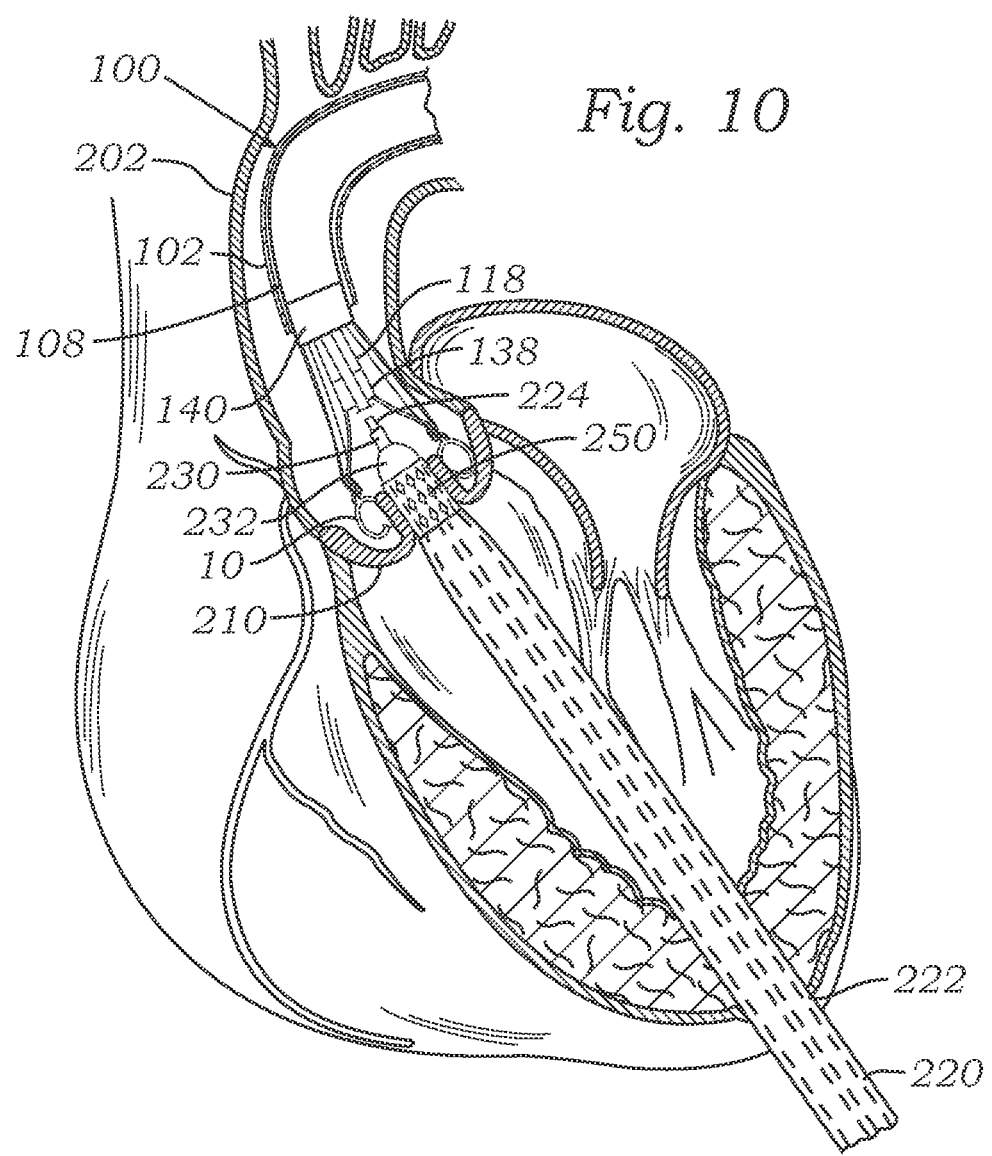
Figure 11:
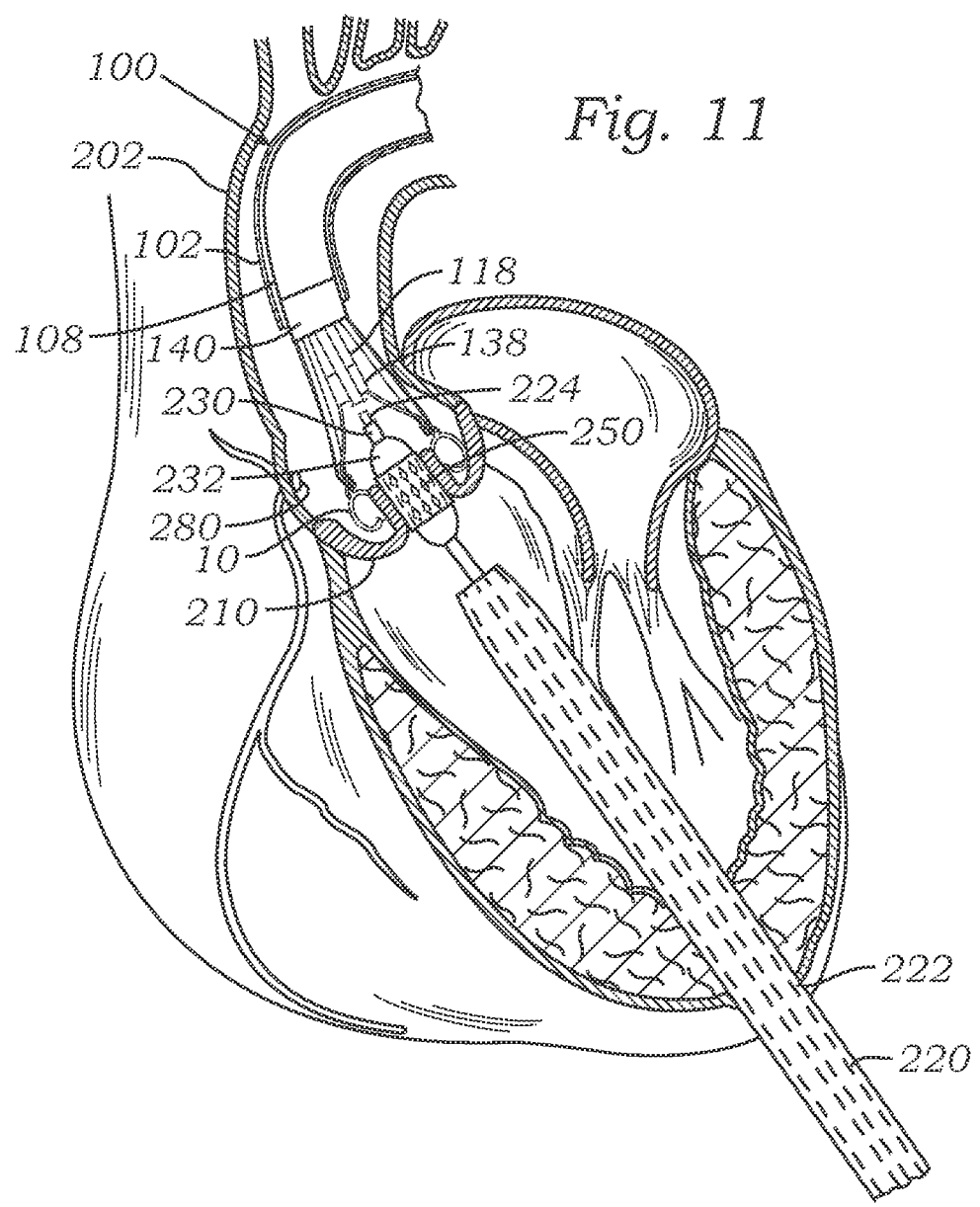
Figure 12:
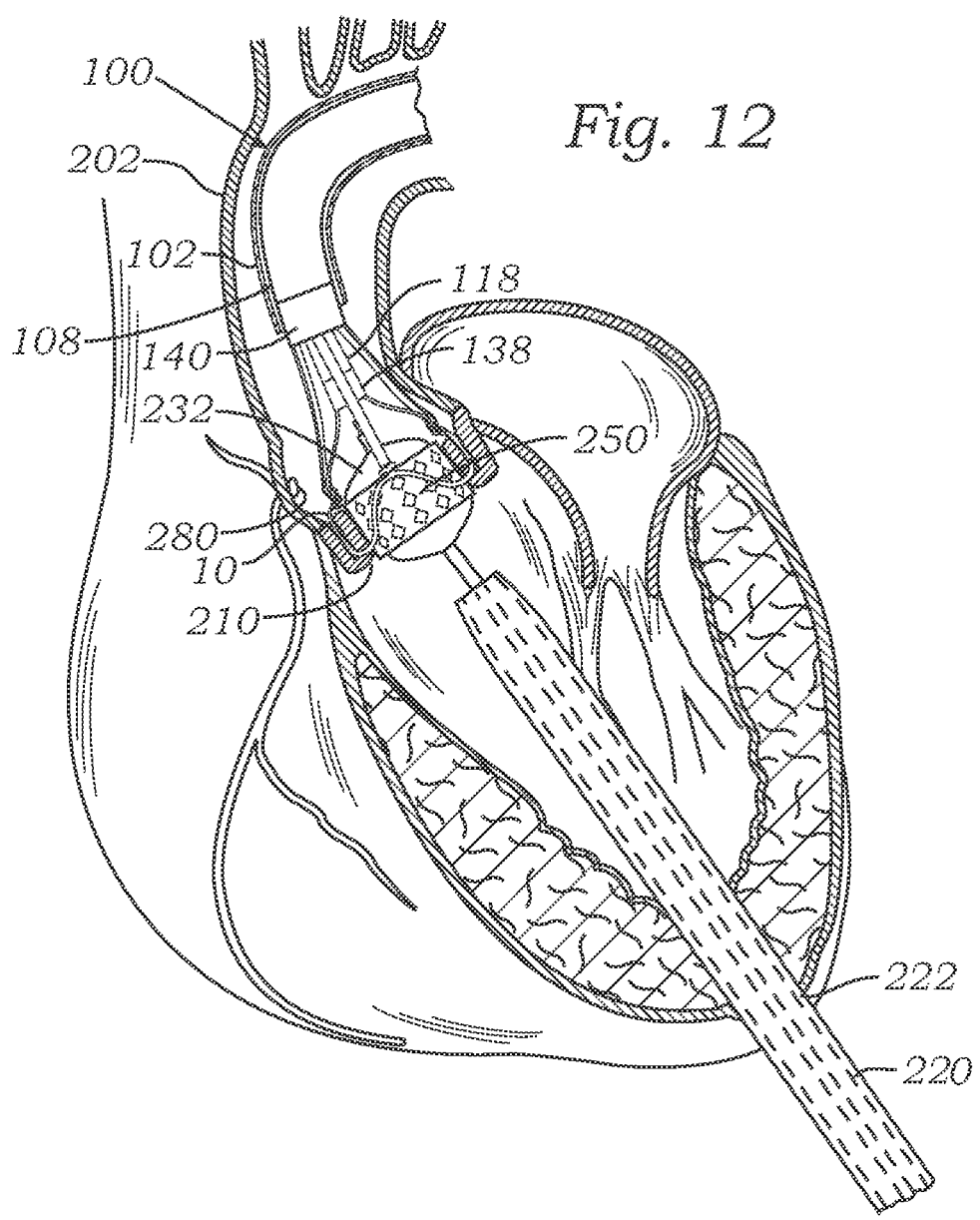
Figure 13:
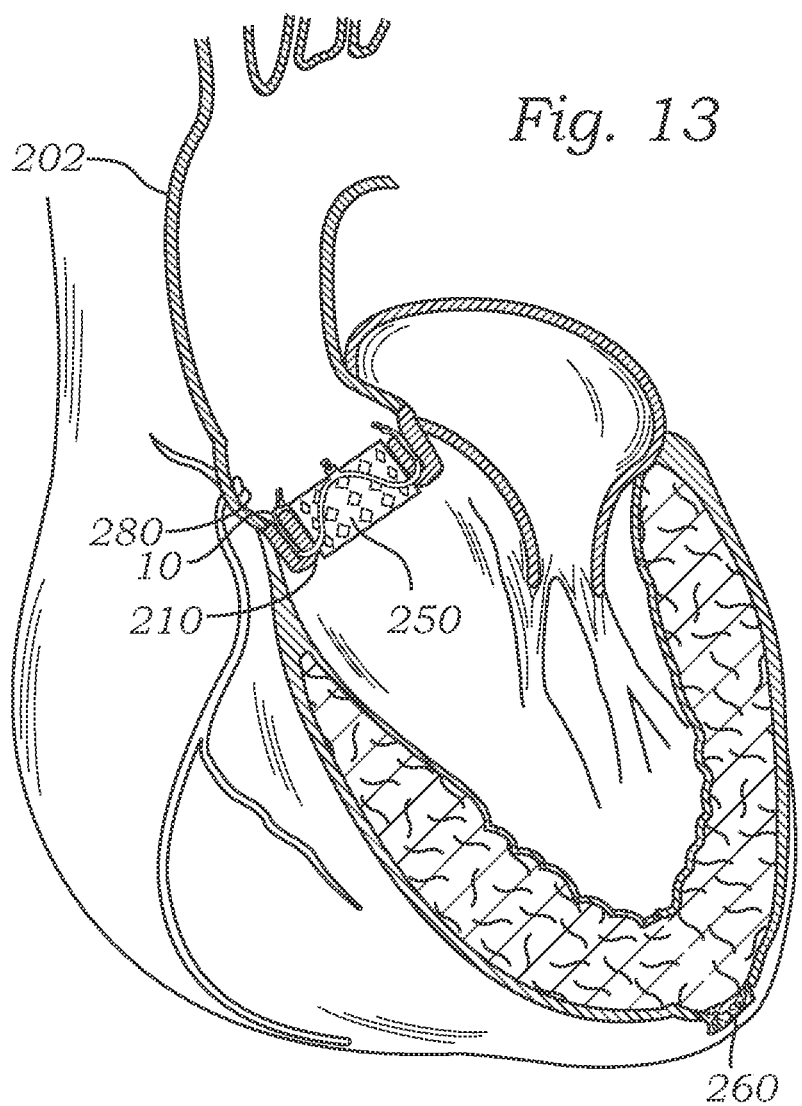

FIG. 10 shows the advancement of the balloon catheter 230 over the guidewire 224 and through the introducer sheath 220. Ultimately, as seen in FIG. 11, the THV 250 is located at the aortic annulus and between the native aortic leaflets. FIG. 11 also illustrates retraction of the introducer sheath 220 from its more distal position in FIG. 10. Radiopaque markers may be provided on the distal end of the introducer sheath 220 to more accurately determine its position relative to the valve 210 and balloon 232. In order to better illustrate the components of the delivery system for the THV, FIGS. 10-11 do not show the front third of the support stent 10 or the corresponding outer and inner prong of the outer fork and the inner fork, respectively. Furthermore, for purpose of illustrating the relative position of the support stent 10 on the THV 250, FIGS. 12-13 show the front third of the support stent 10 and the front of the THV 250, but do not show the portions of the native heart valve that would be secured by the front of the support stent 10. It is to be understood, however, that a corresponding leaflet of the native heart valve would be secured between the support stent 10 and the THV 250.

Again, the precise positioning of the THV 250 may be accomplished by locating radiopaque markers on its distal and proximal ends. In some embodiments, the surgeon can adjust the position of the valve 250 by actuating a steering or deflecting mechanism within the balloon catheter 230. Furthermore, the rotational orientation of the valve 250 can be adjusted relative to the cusps and commissures of the native aortic valve by twisting the balloon catheter 230 from its proximal end and observing specific markers on the valve (or balloon catheter) under fluoroscopy. One of the coronary ostia 280 opening into one of the sinuses of the ascending aorta is also shown in FIG. 11, and those of skill in the art will understand that it is important not to occlude the two coronary ostia with the prosthetic valve 250.

FIG. 11 shows the THV 250 in its contracted or unexpanded state crimped around the balloon 232. When the surgeon is satisfied of the proper positioning and rotational orientation of the valve 250, the balloon 232 is expanded to engage the support stent 10 as seen in FIG. 12. The engagement of the support stent 10 to the exterior of the THV 250 pinches the leaflets of the aortic valve between the support stent and the THV 250, and thereby secures the THV within the annulus of the aortic valve. Once secured into this position, the inner catheter 118 of the delivery system 100 can be retracted, thereby causing the prongs of the inner fork 138 to become disengaged from the retaining arms of the support stent 10. Once the prongs of the inner fork 138 are disengaged, the prongs of the outer fork 140 can be disengaged from the retaining arms by retracting the stent delivery catheter 108. Once disengaged from the support stent, the delivery system 100 can be retracted from the aortic arch and removed from the patient.

It should be noted that the valve 250 can take a variety of different forms and may comprise an expandable stent portion that supports a valve structure, such as one or more leaflets sutured or otherwise secured to the stent or frame of the valve 250. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730,118 and 6,893,460, both of which are hereby expressly incorporated herein by reference.

Once the valve 250 is properly implanted, as seen in FIG. 13, the balloon 232 is deflated, and the entire delivery system including the balloon catheter 230 is withdrawn over the guidewire 224. The guidewire 224 can then be withdrawn, followed by the introducer sheath 220. Ultimately, purse-string sutures 260 at the left ventricular apex can be cinched tight and tied to close the puncture.

Figure 14:
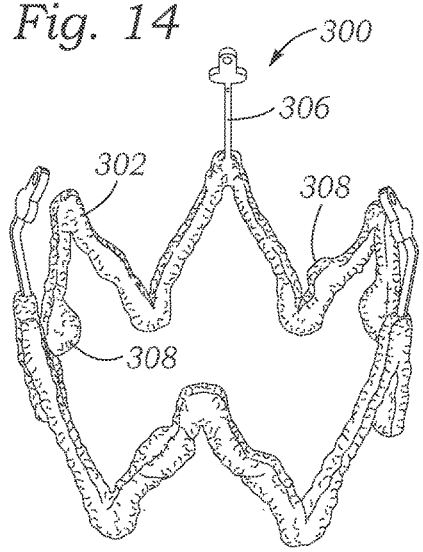
FIGS. 14-15 are perspective views of a support stent, according to another embodiment.
Figure 15:
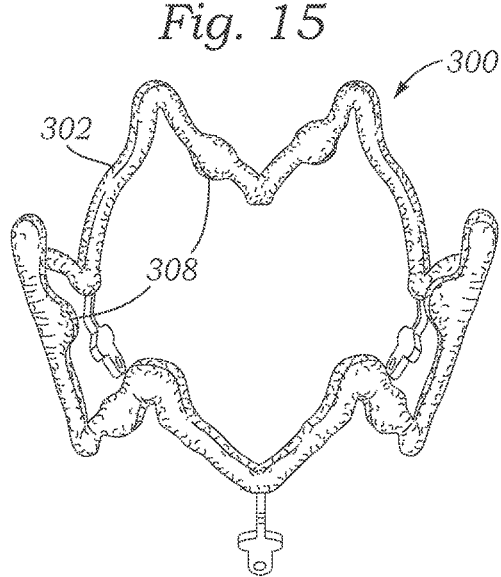
Figure 16:
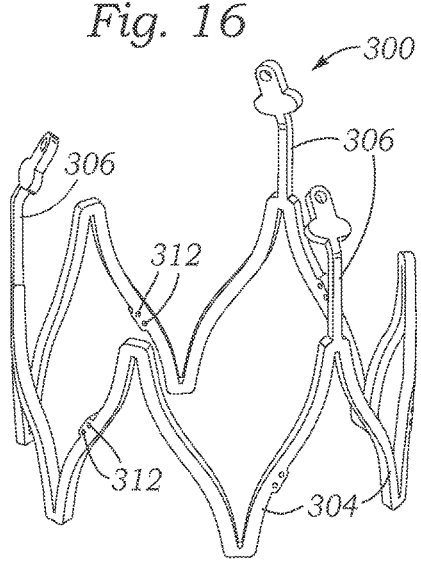
FIGS. 16-17 are perspective and side elevation views, respectively, of the support stent of FIGS. 14-15 shown with the fabric cover removed for purposes of illustration.
Figure 17:
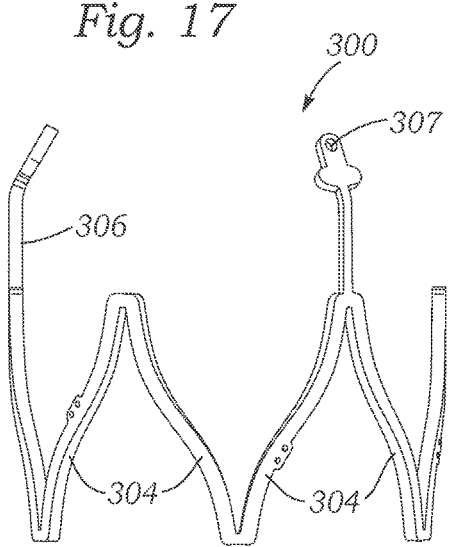

FIGS. 14 and 15 are perspective views of a support stent 300, according to another embodiment. The support stent 300 in the illustrated configuration comprises a plurality of struts arranged in a zig-zag pattern to form an annular body having a plurality of peaks and valleys: six peaks and six valleys in the illustrated embodiment. The stent can include a cover 302, which can be a cloth or fabric covering and extending around the struts of the support stent. The cover 302 can be sutured or otherwise secured to the struts of the stent. The cover 302 can be made from, for example, a fabric (e.g., polyethylene terephthalate (PET)) (sold under the tradename Dacron®), ultra high molecular weight polyethylene (UHMWPE) (sold under the tradename Dyneema Purity®), etc.), tissue (e.g., pericardial tissue), sponge, or a non-woven polymeric material such as silicone. FIGS. 16 and 17 show the support stent 300 without the cover 302 for purposes of illustration. The support stent 300 in the illustrated embodiment comprises a single band, or hoop, comprised of a plurality of angled struts 304 arranged in a zig-zag pattern. The support stent 300 can further include one or more retaining arms 306 (e.g., three equally spaced retaining arms 306 in the illustrated embodiment) extending from the apices of the struts 304 at one end of the band. The retaining arms 306 can be used to form a releasable connection with the distal end of a delivery apparatus, as previously described. Mounted to the inner surfaces of the struts 304 are one or more projections, or protrusions, 308 (also referred to as nubs), that assist in retaining a THV 250 in the implanted position within the interior of the support stent 300, as further described below.

The protrusions 308 can take any of various forms. In the embodiment of FIGS. 14 and 15, the protrusions 308 are formed by securing a knotted or wound ball 310 (FIG. 19) of suture material (or similar type of elongated material) to the inner surfaces of the struts 304, which are then covered by the fabric cover 302. As shown in FIGS. 16 and 17, every other strut 304 is formed with a pair of openings 312 so that a respective suture ball 310 can be tied to each of those struts. It should be understood, however, that a pair of openings 312 can be formed in every strut 304, or in fewer than every strut 304, at one or more selected locations. Also, a strut 304 can have more than one pair of openings 312 to allow more than one suture ball 310 to be secured to that strut. The protrusion 308 can be formed by knotting, braiding, and/or winding any of various types of string, yarn, thread, chord, suture material, or other type of elongate material into the shape of, for example, a ball or sphere.

Figure 20:
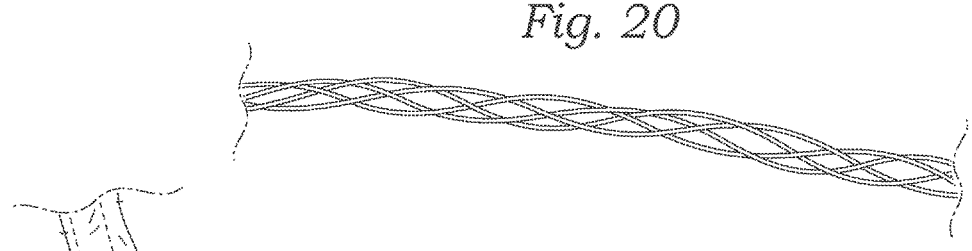
FIGS. 19-21 illustrated a method for forming a suture ball and securing it to the support stent, thereby forming a projection.
Figure 18:
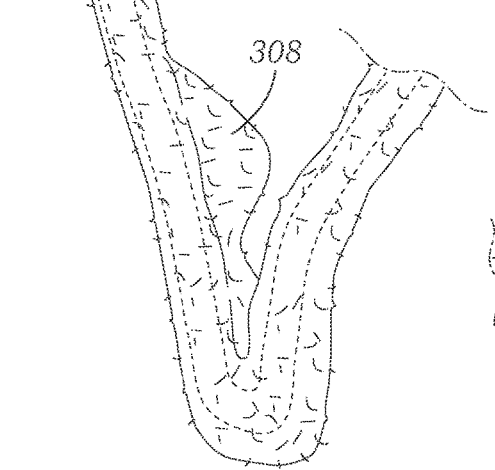
FIG. 18 is an enlarged view of a portion of the support stent of FIGS. 14-15 showing a projection of the support stent.
Figure 21:
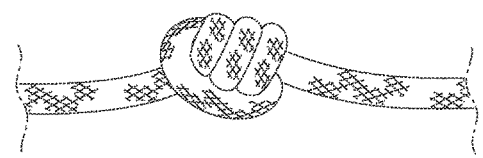
Figure 19:
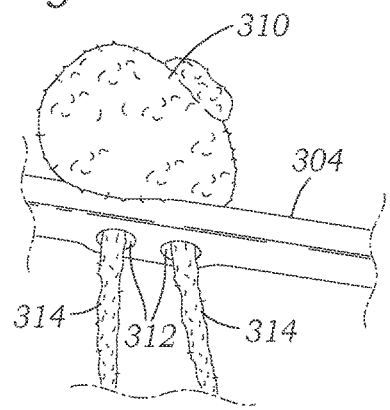
Figure 22:
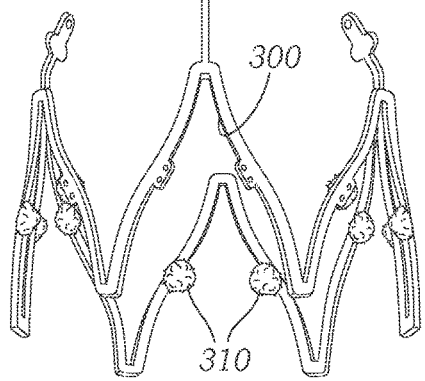
FIG. 22 is a perspective view of the support stent having a plurality of suture balls secured to the stent.

In particular embodiments, the protrusion comprises a suture ball 310, which can be formed by, for example, knitting, or braiding suture material into a length of multi-stranded suture knit or braid, as shown in FIG. 20. A triple wrap knot can then be formed in the suture knit, which for purposes of illustration is shown formed in a length of cord in FIG. 21. The suture knit can be cut on opposite sides of the knot and then unraveled to form a knot 310 with two suture tails 314 extending from the knot 310 (FIG. 19). As shown in FIG. 19, the suture tails 314 can be threaded through respective openings 312 and tied to each other so as to secure the suture ball 310 to the strut 304. FIG. 22 shows the support stent 300 after several suture balls 310 have been tied to the struts 304 of the stent. After the desired number of suture balls 310 have been secured to the stent 300, the struts 304 and the suture balls 310 can be covered with the cover 302 using known techniques.

Moreover, it should be understood that other techniques or mechanisms can be used to secure the suture balls 310 to the struts. For example, one or more selected struts 304 can have a single opening 312 for tying a respective suture ball 310 to each of those struts. In another implementation, the sutures 314 can be tied around the outside or perimeter of a strut 304. In another implementation, the suture balls 310 can be secured to the struts using an adhesive.

Preferably, although not necessarily, the projections 308 are positioned along the inner surfaces of the struts 304 so that they can extend through openings in the cells of the frame of a THV 250 when the support stent is implanted. FIG. 23 shows the support stent 300 placed around a stent, or frame, 350 of a THV. For purposes of illustration, the prosthetic leaflets of the THV (which are secured to the inside of the frame 350) and the leaflets of the native valve are not shown in FIG. 23. Typically, the leaflets of the native valve are interposed between the frame 350 and the support stent 300 after implantation, as previously described. As shown, the frame 350 comprises a plurality of struts 352 arranged to form a plurality of openings 354 at the outflow end of the frame and a plurality of larger openings 356 at the inflow end of the frame. The projections 308 desirably are positioned such that when the support stent 300 is positioned around the frame 350, the projections 308 extend through respective openings 354, 356 in the frame. FIG. 24 shows the support stent 300 implanted on the outside of a THV 250 with the native leaflets 210 of the aortic valve interposed and pinched between the support stent 300 and the THV. The forward half of the support stent 300 is removed in this view for purposes of illustration. As depicted in FIG. 24, the projections 308 extend radially inwardly into the openings of the THV's frame, thereby pressing portions of the native leaflets 210 into the openings of the THV's frame (e.g., openings 354, 356 in FIG. 23). The action of the projections 308 pressing the native leaflets 210 inwardly into the openings of the frame increases the retention force of the support stent against the THV 250, and therefore better resists dislodgement of the THV. In this manner, the projections 308 function as an interlocking feature to assist in retaining the THV in the implanted position.

FIG. 25 is a flattened view of the frame 350 superimposed on top of the support stent 300. FIG. 25 shows the desired position of the support stent 300 relative to the frame 350 when both components are implanted, although both components are shown in a flattened or unrolled configuration for purposes of illustration. The suture balls 310 can be positioned at any locations on the struts 304 that would allow the suture balls 310 to project inwardly into the openings 354, 356 of the frame 350. FIG. 26 is a flattened view of a frame 360, according to another embodiment, superimposed on top of the support stent 300. The frame 360 in this embodiment has a first row of openings 362 at the outflow end of the frame, a second, intermediate row of openings 364, and a third row of openings 366 at the inflow end of the frame. The suture balls 310 can be positioned at any locations on the struts 304 that would allow the suture balls 310 to projection inwardly into one or more of openings 362, 364, 366 of the frame 360.

In particular embodiments, the diameter of the suture ball 310 is from about 1.4 mm to about 1.9 mm, although the size of an individual suture ball can vary depending on the application and various factors, such as the size of the openings in the THV's frame and the total number of suture balls secured to the stent.

Figure 27:
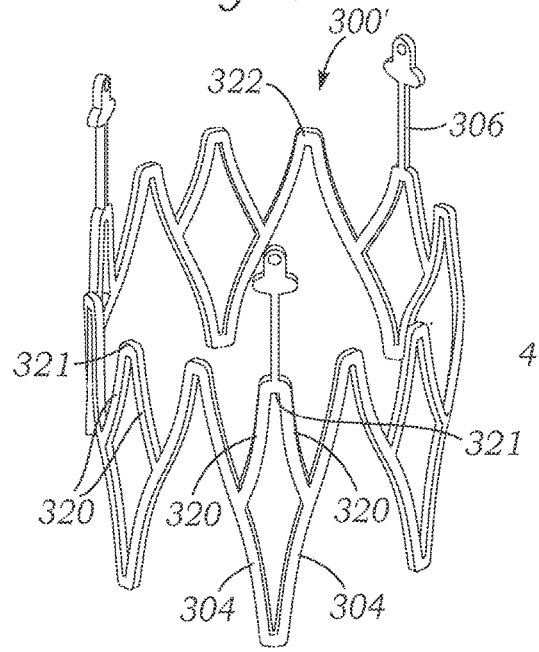
FIG. 27 is a perspective view of another embodiment of a support stent.

FIG. 27 is a perspective view of a support stent 300', according to another embodiment. The support stent 300' is similar to support stent 300, except that the support stent 300' includes additional struts 320 arranged in pairs between pairs of struts 304. Each strut 320 has one end connected to a strut 304 (e.g., at about the mid-point of the strut 304) and another end connected to the end of an adjacent strut 320 to form an apex 321. The retaining arms 306 can extend from respective apices 321. Each pair of struts 320 forms a closed, diamond-shape cell with portions of a respective pair of struts 304. The diamond-shape cells increase the radial strength of the support stent 300', and therefore can increase the retention force against a THV mounted within the support stent 300'. Although not shown, the apices 321 and/or the apices 322 between struts 304 can be bent or can be curved inwardly toward the central flow axis of the support stent to increase the retention force against a THV implanted within the support stent 300'. The support stent 300' optionally can include projections 308 (such as suture balls) and a cover 302, similar to the support stent 300.

Figure 28:
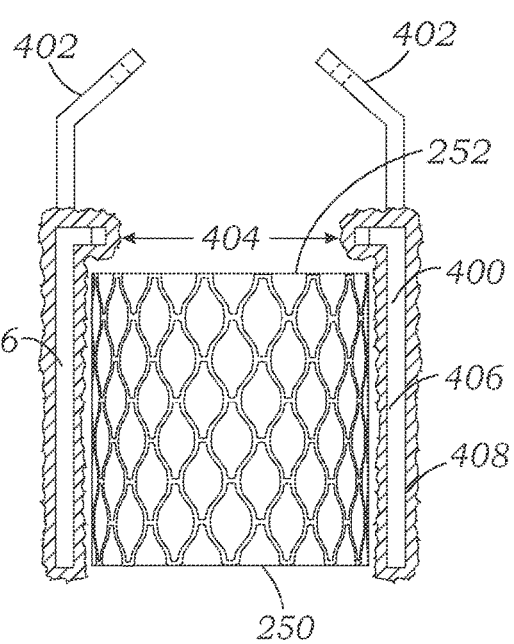
FIG. 28 shows another embodiment of a support stent and a prosthetic valve implanted within the support stent.
Figure 29:
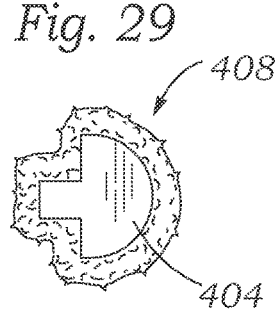
FIG. 29 is an enlarged top plan view of a projection of the support stent of FIG. 28.

FIG. 28 is a cross-sectional view of a support stent 400, according to another embodiment. The support stent 400 can comprise multiple struts that can be arranged in a configuration similar to FIGS. 16-17. Multiple retaining arms 402 can extend from one end of the support stent 400. The support stent 400 includes multiple projections 404 circumferentially spaced around one end of the stent. The projections 404 in the illustrated embodiment extend radially inwardly and are perpendicular to the longitudinal flow axis of the support stent. Each projection 404 can be an extension of a strut 406 and can be bent inwardly relative to the strut 406 during the manufacturing process. FIG. 29 shows a top plan view of a single projection 404. The support stent can further include a cover 408 (e.g., a fabric cover) covering the struts 406 and the projections 404. As shown in FIG. 28, the THV 250 can be implanted such that its outflow end 252 is adjacent the lower surfaces of the projections 404. In this manner, the projections 404 can resist dislodgement of the THV 250 in the direction of the flow of blood toward the aorta, and/or position the THV 250 during deployment thereof. In another implementation, the THV can be implanted relative to the support stent 400 such that the projections 404 can extend into the openings of the frame of the THV.

FIGS. 30-48 show various ways that a projection can be formed on or mounted to a strut of a support stent, such as support stent 300. Although not shown, any of the embodiments described below can include a cover (e.g., cover 302) that covers the stent and the projections formed on or mounted to the stent. FIGS. 30 and 31 show perspective assembled and exploded views of a separately formed projection member 602 configured to be mounted on a strut 600 of a support stent. The projection member 602 includes a base 604 and a projection 606 extending from the base. The base 604 can be configured to form a snap-fit connection with the strut 600, or alternatively, can be welded or adhesively secured to the strut 600. The base 604 and the projection 606 can be made from any of various suitable materials, such as metals (e.g., stainless steel) or any of various elastomeric or non-elastomeric polymers (e.g., polyurethane, nylon, silicone).

FIGS. 32-33 show a strut 610 of a support stent. The strut 610 has a main strut body 612 and first and second laterally extending arms 614, 616. The arms 614, 616 can be bent or folded along fold lines 618 so that arm 616 is folded on top of arm 614 to effectively form a projection extending from the strut 610.

FIG. 34 shows a strut 620 formed with an opening 622. A projection 624 can be secured to the strut 620 by inserting a pin 626 of the projection 624 into the opening 622. The projection 624 can be welded to the strut 620, secured to the strut 620 with a suitable adhesive, peened, swaged or deformed to create an interference fit with the opening 622, and/or the projection 624 can be sized to form a friction fit with the opening 622. The projection 624 can be made from any of various suitable materials, such as metals (e.g., stainless steel) or any of various elastomeric or non-elastomeric polymers (e.g., polyurethane, nylon, silicone).

FIG. 35 shows a projection 630 in the form of a small sphere or bead having an opening 632 extending therethrough. The projection 630 can be secured to a strut 634 using a suture 636 extending through the opening 632 in the projection and an opening 638 in the strut 634. The suture 636 can be tied off or knotted at its opposite ends to secure the projection 630 in place. FIG. 36 shows a projection 630 tied to a strut 640 by a suture 642 that extends through the opening 632 in the projection and wraps around the strut 640. The strut 640 can include a recessed or narrowed portion 644 around which the suture 642 is wrapped to prevent the projection from sliding along the length of the strut. The projection 630 can be made from any of various suitable materials, such as metals (e.g., stainless steel) or any of various elastomeric or non-elastomeric polymers (e.g., polyurethane, nylon, silicone).

FIG. 37 shows a projection 650 formed from multiple layers 652 of material, such as layers of fabric (such as used to form the cover 302 of the stent), stacked on top of each other. The material layers 652 can be tied to a strut 654 by a suture 656 extending through the material layers 652 and corresponding openings in the strut 654. In some embodiments, the projection 650 comprises a single layer 652 of material, for example, metal, polymer, fabric, sponge, or silicone, tied to the strut 652.

FIG. 38 shows a strut 660 formed with a shape set projection 662. In this embodiment, the strut 660 and the projection 662 can be formed from a suitable self-expanding or shape-set material, such as nitinol. The projection 662 can be folded against the strut 660 during delivery of the support stent. When the support stent is radially expanded (such as after being deployed from a delivery sheath), the projection 662 can pivot outwardly relative to the strut 660 to the position shown in FIG. 38.

FIG. 39 shows a projection in the form of a rivet 670 comprising a head portion 672 and a pin 674. The pin 674 can be inserted into an opening 682 of a strut 680 and secured in place by bending or deforming the end portions 676 of the pin 674, as depicted in FIG. 40. The rivet 670 can be made of any of various biocompatible metals, such as stainless steel, or other malleable materials.

FIGS. 41 and 42 show a projection 690 formed by molding a polymer on a strut 692. The molded projection 690 can have a inwardly facing projection portion 694 (which contacts the native leaflets when implanted), an intermediate portion 696 formed in an opening extending through the strut 692, and an outwardly facing projection portion 698 that has a diameter greater than that of the opening in the strut to retain the projection in place against the strut. The projection 690 can be made from any of various elastomeric or non-elastomeric polymers (e.g., polyurethane, nylon, silicone).

FIG. 43 shows a projection 700 in the form of a ball of cloth that can be tied to a strut 702 with a suture 704.

FIG. 44 shows a projection 710 in the form of a cylindrical body 710. The projection 710 can be tied to a strut 712 by a suture 714 that extends through the body 710 and openings in the strut. The projection 710 can be made from any of various suitable materials, such as metals (e.g., stainless steel) or any of various elastomeric or non-elastomeric polymers (e.g., polyurethane, nylon, silicone).

FIGS. 45 and 46 show a projection 716 configured to be mounted on a strut 718 of a support stent. The projection 716 can be shaped so as to form a three-sided channel 720 through which a portion of the strut 718 extends. The projection 716 can be formed from an elastomeric material, such as silicone, to provide the support stent with a greater gripping force against the native leaflets and a THV deployed within the native leaflets. The projection 716 can be formed with bristles 720 that can contact the native leaflets when implanted. The bristles 720 can further enhance the gripping force of the support stent against the native leaflets. The projection 716 can be secured to the strut 718, such as with an adhesive or molding the projection to the strut. In other embodiments, the projection 716 can be made of metal and can be welded to the strut.

FIG. 47 shows a projection 730 in the form of a rivet that can be secured within an opening 732 of a strut 734. The projection 730 can include an enlarged head portion 736 (which contacts the native leaflets when implanted), a shaft 738 and a retaining member 740. The projection 730, or at least the retaining member 740, can be made of an elastomeric and/or resilient material (e.g., polyurethane, nylon, silicone), so that the retaining member can be radially compressed and pressed through the opening 732 in the strut and then can expand back its normal size and shape when it passes through the opening. When installed on the strut, the retaining member 740 is on the opposite side of the strut from the head portion 736 and therefore retains the projection in place. The head portion 736 can be any of various shapes, such as a sphere or a portion of a sphere. FIG. 48 shows a similar projection 730' having a head portion 736' shaped as a cube.

Figure 49:
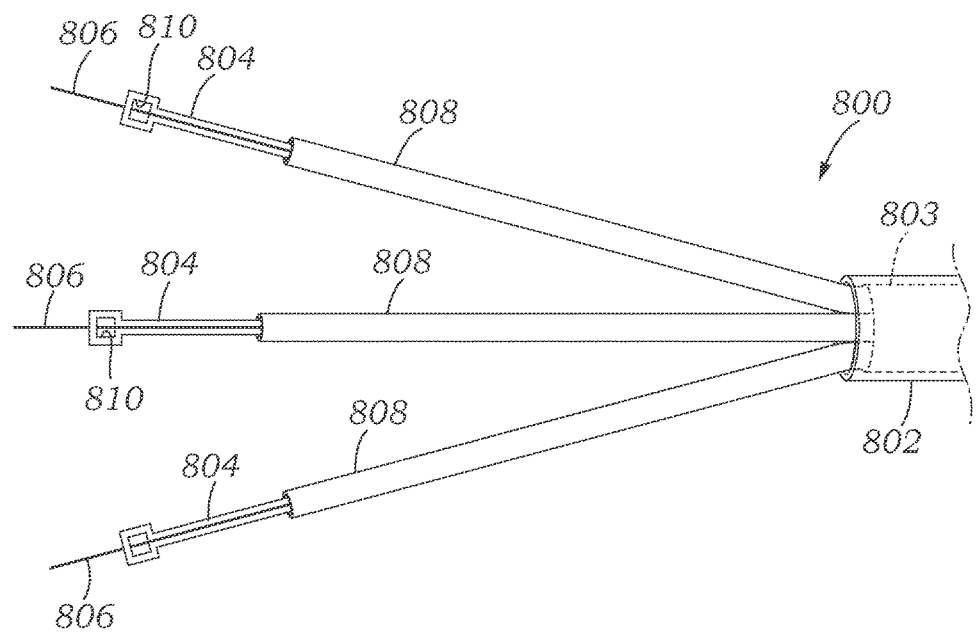
FIG. 49 shows the distal end portion of a delivery apparatus that can be used to implant a support stent, according to one embodiment.

FIG. 49 shows the distal end portion of a delivery apparatus 800 for implanting a support stent, such as support stent 10 or 300. The delivery apparatus 800 comprises an outer shaft or sheath 802 from which a plurality of attachment arms 804 extend. Each attachment arm 804 is paired with a respective release wire 806, which together form a releasable connection with a respective retaining arm of a support stent (e.g., retaining arms 306 of the support stent 300). The illustrated embodiment includes three pairs of attachment arms 804 and release wires 806 to correspond with the three retaining arms 306 of the support stent 300. The attachment arms 804 can be connected to an inner shaft, or pusher member, 803 that extends coaxially through the outer shaft 802. The release wires 806 can extend alongside or through the inner shaft 803 the length of the delivery apparatus to a handle (not shown) for manipulation by a user. Alternatively, the release wires 806 can be connected to another shaft or a common pull wire that extends through or alongside the inner shaft 803 such that all three release wires can be move together by moving the additional shaft or pull wire.

A respective sheath 808 extends over each pair of an attachment arm 804 and a release wire 806. The sheaths 808 prevent the release wire 806 from kinking when the support stent is being deployed inside the body and when the pull wire is retracted to release the support stent, as further described below. During delivery of a support stent 300, the support stent, the attachment arms 804 and the release wires 806 are contained within the sheath 802. When the support stent is at or adjacent the implantation site, the support stent, the attachment arms, and the release wires can be advanced from the distal opening of the sheath 802, as depicted in FIG. 49.

The attachment arms 804 and release wires 806 can be connected to the retaining arms 306 of the support stent much like the inner and outer forks 138, 140, respectively, described above. Referring to FIGS. 50 and 51, the upper end portion of a retaining arm 306 is inserted through an opening 810 of an attachment arm 804. The distal end portion of a release wire 806 is then inserted through an opening 307 in the retaining arm 306. The release wire 806 prevents the retaining arm 306 from disconnecting from the attachment arm 804 until the release wire is retracted from the opening 307. As shown in FIGS. 50-51, the attachment arm 804 and the release wire 806 are relatively flexible and bow outwardly when advanced from the sheath 802 during deployment of the support stent 300. Hence, as shown in FIGS. 52 and 53, the sheath 808 extends over the attachment arm 804 and the release wire 806 and keeps them in close proximity to prevent the release wire 806 and the attachment arm 804 from kinking and/or bowing outwardly relative to each other when advanced from the main sheath 802 and when the pull wire is retracted to release the support stent.

In particular embodiments, two separate delivery systems can be used to at least partially simultaneously deliver a support stent and a prosthetic heart valve to the outflow side of the aortic arch. For illustrative purposes, such dual system approaches are described with respect to approaches that at least partially simultaneously approach the outflow side of the aortic valve (e.g., through the ascending aorta), although similar techniques can be used to deploy the support stent and the prosthetic heart valve from the inflow side of the aortic valve.

When delivering the support stent and the prosthetic heart valve transfemorally using two separate delivery systems, access to the aortic valve can be obtained through different access routes or points. For example, the support stent delivery system can be delivered through the left femoral artery while the prosthetic heart valve delivery system can be delivered through the right femoral artery, or vice versa. In other embodiments, the support stent delivery system can be delivered through the carotid artery (e.g., through the right carotid artery and into the brachiocephalic artery or through the left carotid artery) or through the subclavian artery (e.g., through the right subclavian artery and into the brachiocephalic artery or through the left subclavian artery) and toward the outflow side of the aortic valve while the prosthetic heart valve delivery system can be delivered transfemorally (e.g., through the left or right femoral artery), or vice versa. Using the carotid or subclavian arteries can provide a more direct approach to the aortic valve than through a femoral artery and over the aortic arch, thus making such an approach potentially more desirable for delivering the support stent or prosthetic heart valve.

Figure 54:
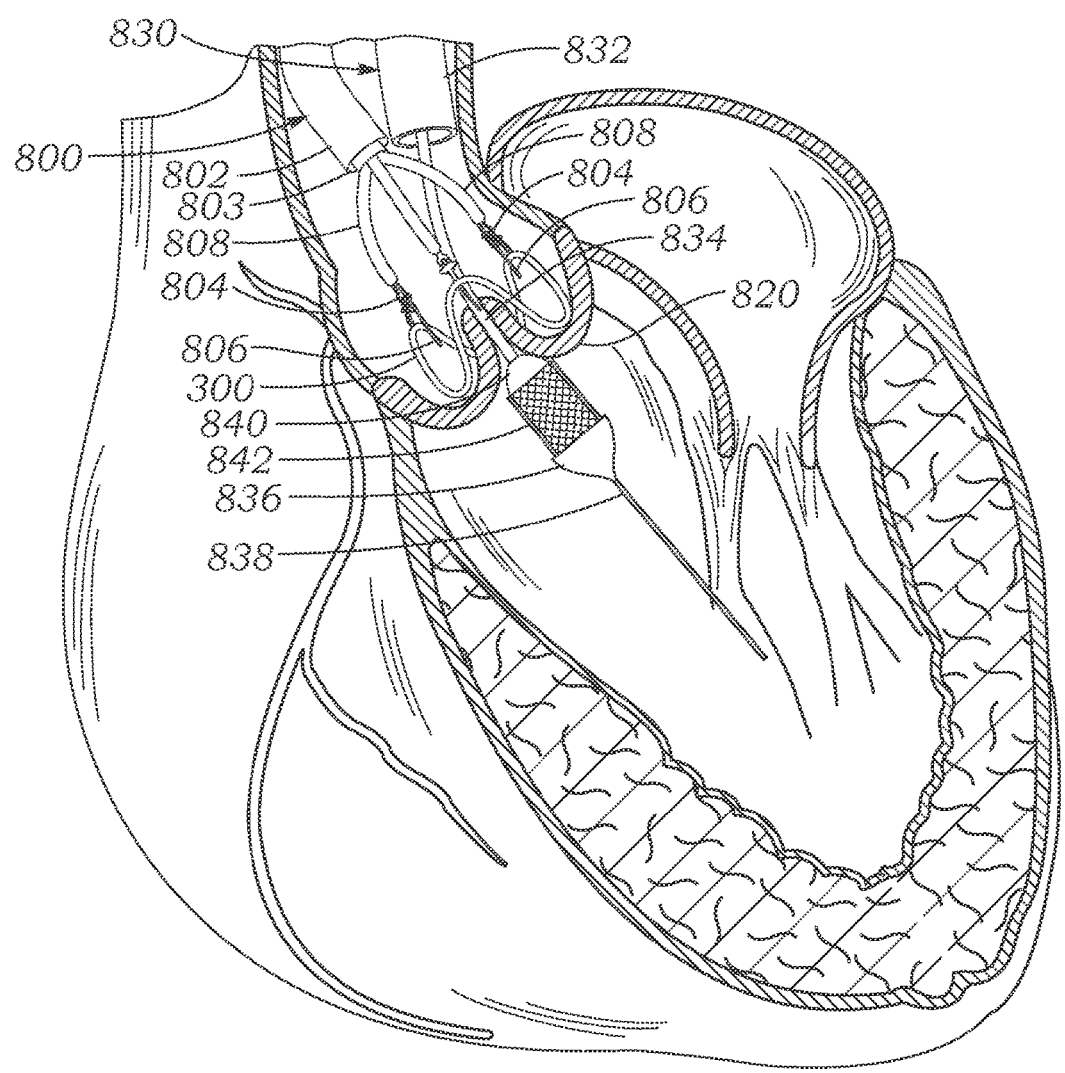
FIG. 54 is a cross-sectional view of an aortic valve illustrating an exemplary procedure for deploying a support stent around a prosthetic heart valve using a dual system approach.

FIG. 54 illustrates one exemplary system and procedure for deploying the support stent and securing a prosthetic valve to the support stent using a multi-system approach where the multiple delivery systems are at partially simultaneously advanced toward the outflow side of the aortic valve. In particular, FIG. 54 is a cross-sectional view through the left side of a patient's heart showing acts performed in delivering a support stent 300 from the outflow side of the aortic valve.

FIG. 54 shows a main catheter 802 of a support stent delivery system 800 as it is advanced into a position near the surface of the outflow side of the aortic valve 820. The support stent delivery system 800 can be inserted through one of the femoral arteries of the patient or through one of the carotid or subclavian arteries, and advanced into the aorta in the retrograde direction. FIG. 54 also shows a main catheter 832 of a prosthetic heart valve delivery system 830. The prosthetic valve delivery system 830 can be inserted through another one of the femoral arteries of the patient or through the carotid or subclavian arteries (if the support stent delivery system 800 is advanced transfemorally) and also advanced into the aorta in the retrograde direction. FIG. 54 additionally shows attachment arms 804, release wires 806, and the sheaths 808 extending from the distal opening of the main shaft 802 and coupled to respective retaining arms of the support stent 300. FIG. 54 further shows a prosthetic valve delivery catheter 834 (a balloon catheter in the illustrated embodiment), nose cone 836, and guidewire 838, which is shown as being extended through the aortic valve 820. In the illustrated embodiment, the prosthetic valve delivery catheter 834 is advanced to the point where a balloon portion 840 around which the prosthetic valve 842 is compressed and nose cone 836 are located adjacent to an inflow side of the native leaflets of the aortic valve. Furthermore, in FIG. 54, the inner shaft 803 is advanced from the outer shaft 802, allowing the support stent 300 to expand into its uncompressed, natural shape in a position above the aortic valve 820.

In order for the prosthetic valve delivery catheter 834 to be advanced through the aortic valve as shown, the attachment arms 804, the release wires 806, and the sheaths 808 are desirably configured so that they arch radially outward from the end of the inner shaft 803. The sheaths 808 keep the release wires in close alignment with their respective attachment arms and keep the release wires from kinking when they are moved to release the support stent. Together, the attachment arms 804, the release wires 806, and the sheaths 808 can be said to form a globe-like or pumpkin-like shape. This shape increases the space between the pairs of attachment arms and release wires, and creates a sufficient opening through which the nose cone 836, balloon portion 840, prosthetic valve 842, and prosthetic valve delivery catheter 834 can be advanced into the illustrated position.

Deployment of the prosthetic valve 842 can be achieved by positioning the prosthetic valve between the native leaflets of the aortic valve and inflating the balloon 840, causing the prosthetic valve to radially expand until the native leaflets are pinched between the support stent 300 and the prosthetic valve. The prosthetic valve delivery system 830 can then be retracted to remove the balloon catheter 834 from the space between the attachment arms. The support stent 300 can then be released from the support stent delivery system 800 by retracting the release wires 806.

It should be understood that the exemplary systems shown in FIG. 54 are by way of example and that any suitable support stent delivery system disclosed herein or suitable prosthetic heart valve delivery system disclosed herein can be used as part of a dual system delivery method.

As illustrated by the various delivery systems and approaches described in this disclosure, there are many delivery options available to both the patient and the physician for delivering a prosthetic heart valve secured by a support stent. In order to determine which of the systems and approaches is most suitable for a particular patient, the patient can be screened. For example, the patient can be screened for vasculature tortuosity and/or apical integrity. Depending on the patient etiology, a transfemoral approach may be a more appropriate mode of delivering the devices, or vice versa.

Figure 55A:
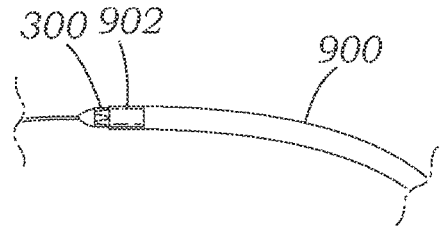
FIGS. 55A-55E are side views of the distal end portion of a delivery apparatus illustrating premature deployment of a support stent caused by changing the curvature of the delivery apparatus.
Figure 55B:
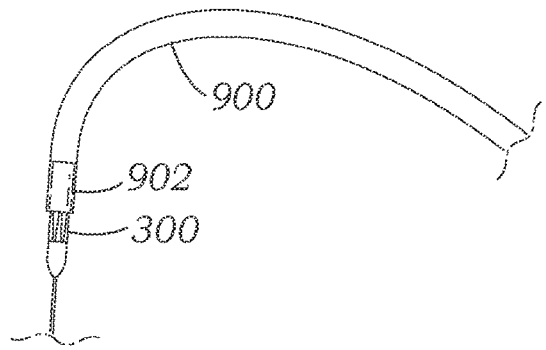
Figure 55C:
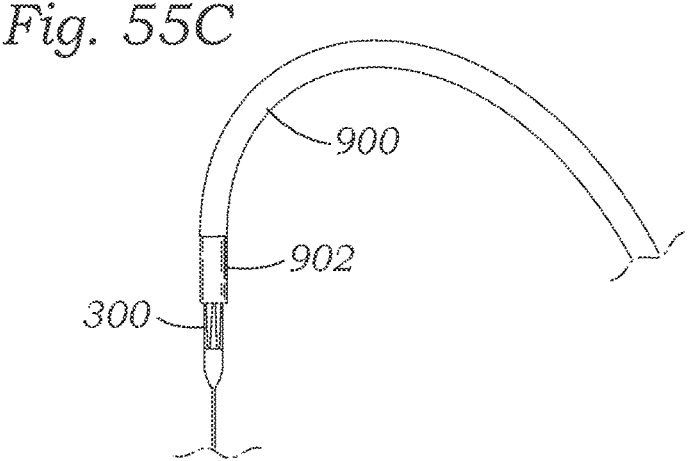
Figure 55D:
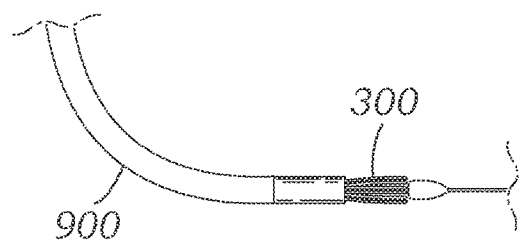
Figure 55E:
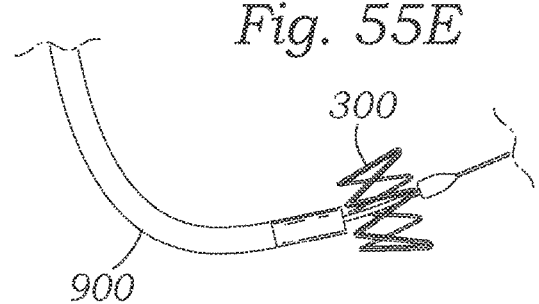

FIG. 55A shows the distal end portion of a delivery apparatus comprising a steerable outer shaft 900, the distal end portion of which comprises a sheath 902 for containing an expandable implant, such as the illustrated support stent 300. The support stent 300 can be releasably connected to the distal end of an inner shaft (not shown) via an attachment assembly or mechanism, such as the attachment arms 804 and release wires 806, as described above. The inner shaft (also referred to as a "pusher member") extends coaxially through the outer shaft and has a proximal end portion coupled to a handle mechanism (not shown). The outer shaft 900 contains one or more pull wires to control the curvature of the delivery apparatus as it is advanced through the aortic arch, as is well known in the art.

As discussed above, the support stent 300 can have one or more projections 308 (FIG. 14). The portion of the support stent without any projections 308 may be radially compressible to a smaller diameter than the portion of the support stent having the projections 308. Consequently, as shown in FIG. 55A, the support stent 300 can be crimped and loaded into the sheath for delivery into a patient's vasculature such that the portion of the support stent having the projections 308 extends outwardly from the sheath. In this manner, the sheath can be sized for the smallest possible crimped diameter of the support stent (which corresponds to the portion of the support stent 300 without any projections 308) to minimize the overall profile of the delivery apparatus.

In use, when the deflection of the outer shaft is increased, it is subject to compressive forces due to the pull wires, causing the outer shaft to decrease in length. As illustrated in FIGS. 55B-55E, this shortening of the shaft 900 can cause the support stent 300 to prematurely advance from the sheath 902.

Figure 56:
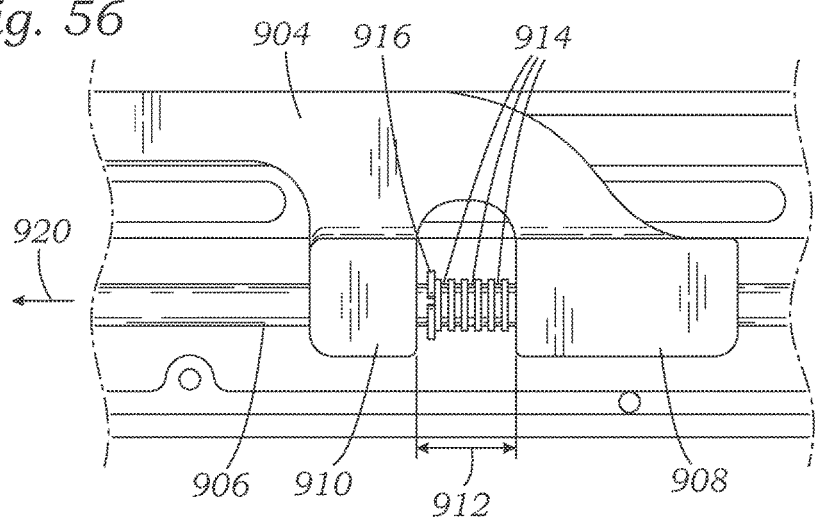
FIG. 56 is an enlarged view of a drive mechanism inside a handle of a delivery apparatus that can prevent premature deployment of a medical implant when the curvature of the delivery apparatus is adjusted.

To prevent such premature deployment of the support stent, the inner shaft can be configured to slide axially relative to the outer shaft 900 as the outer shaft is deflected by the pull wires. In accordance with one embodiment, FIG. 56 shows the internal mechanism of a handle of the delivery apparatus that allows such sliding movement of the inner shaft. As shown, the handle contains a drive mechanism 904 operatively connected to the proximal end portion of an inner shaft 906. The drive mechanism 904 comprises a distal portion 908 spaced from a proximal end portion 910 and a gap 912 between the distal portion and the proximal end portion. The inner shaft 906 extends through and is slidable relative to the distal portion 908 and the proximal portion 910 in the distal and proximal directions. In the space between the distal portion 908 and the proximal portion 910, the shaft 906 has a plurality of axially spaced annular grooves 914. An adjustable stop member, such as in the form of a ring or clip 916, is mounted on the shaft 906 within a selected groove 914 and allows a limited amount of axial movement of the shaft 906 relative the driving mechanism 904 equal to the length of the gap 912. The clip 916 can be a C-shaped clip (i.e., an annular ring having a gap) that can be press fitted onto the shaft 906 within one of the grooves 914.

Figure 57:
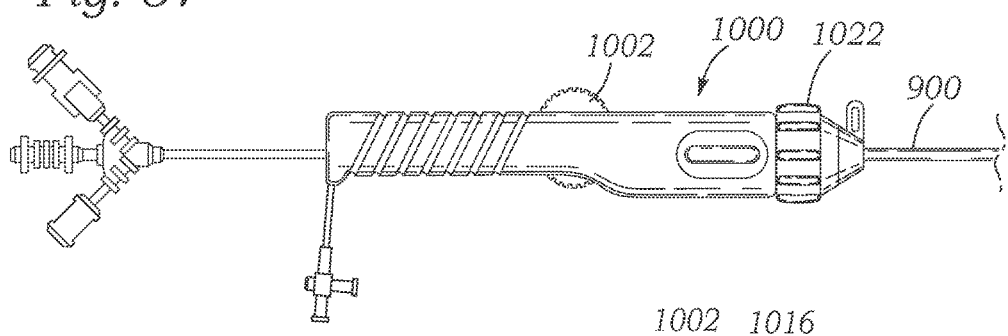
FIG. 57 is a side view of an exemplary handle of a delivery apparatus for a medical implant, such as a support stent.

FIG. 57 shows an exemplary handle 1000 for the delivery apparatus. The proximal end of the outer shaft 900 can be secured to the handle. The proximal end portion of the inner shaft 906 can extend into the handle where it is supported by the drive mechanism 904. The handle 1000 can have an adjustment mechanism 1022 in the form of a rotatable knob that is configured to adjust the curvature of the outer shaft 900. The delivery apparatus can have one or more pull wires that extend longitudinally through the outer shaft and have proximal end portions operatively connected to the adjustment mechanism 1022. Rotation of the knob 1022 is effective to adjust the curvature of the outer shaft by adjusting the tension of the one or more pull wires. Further details of the adjustment mechanism are disclosed in U.S. Patent Application Publication No. 2009/0281619 A1, which is incorporated herein by reference. The distal end of the inner shaft 906 can be releasably connected to a support stent 300, such as through the attachment arms 804 and the release wires 806 (FIG. 49). During delivery through a patient's vasculature, the support stent 300, the attachment arms 804, and the sheaths 808 can be housed in the distal end portion of the outer shaft 900.

In use, as the outer shaft 900 is deflected and slightly foreshortened by the compressive forces on the shaft, the inner shaft 906 (and thus the support stent 300) can slide proximally relative to the outer shaft (in the direction of arrow 920, FIG. 56) to prevent premature exposure of the support stent from the distal sheath 902. Proximal movement of the shaft 906 is limited by contact of the clip 916 against the proximal portion 910 of the drive mechanism. Distal movement of the shaft 906 relative to the outer shaft 900 is limited by contact of the clip against the distal portion 908 of the drive mechanism. When the distal end of the delivery apparatus is at or near the desired deployment location for the support stent within the body (e.g., within the aortic root), the support stent can be deployed from the sheath 902 by moving the drive mechanism distally. As the drive mechanism 904 is advanced, the proximal portion 910 bears against the clip 916, which causes the inner shaft (and thus the support stent 300) to move distally relative to the outer shaft to deploy the support stent from the sheath 902. Conversely, the outer shaft 900 can be retracted proximally relative to the inner shaft 906 and the drive mechanism to deploy the support stent. As the outer shaft 900 is retracted, the clip 916 bears against the distal portion 908 of the drive mechanism to retain the inner shaft 906 in a stationary position relative to the drive mechanism.

Also, due to manufacturing constraints, the overall lengths of the outer shaft 900 and the inner shaft 906 can vary slightly amongst individual delivery apparatuses. For example, the steerable outer shaft of the delivery apparatus can be purchased from various manufacturers. The overall length of the outer shaft can vary amongst different manufacturers or amongst the same manufacturer. When assembling the delivery apparatus, the inner shaft 906 needs to be axially aligned within the outer shaft such that the support stent 300 can be retained within the distal sheath 902 during the implantation procedure until such time the physician actuates a mechanism on the handle to deploy the stent. During the assembly process, the inner shaft 906 is inserted through the drive mechanism 904 and the axial positioning of the shaft 906 is adjusted until the desired position of the shaft 906 relative the outer shaft is achieved. The clip 916 is then placed on the shaft 906 within a selected groove 914 to retain the proximal end portion of the inner shaft within the handle. As can be appreciated, the multiple grooves 914 on the inner shaft allow the axial positioning of the inner shaft to be adjusted to compensate for any variations in the overall length of the inner shaft and/or the outer shaft.

The handle 1000 in the illustrated embodiment can further include a rotatable knob 1002 that is configured to control the deployment of an implant (e.g., support stent 300) from the sheath of the delivery apparatus (e.g., the distal end portion of the outer shaft 900). For example, the rotatable knob 1002 can be operatively connected to the drive mechanism 904 (FIG. 56) to control distal and proximal movement of the drive mechanism (and thus the inner shaft 906 and the support stent) relative to the outer shaft. For this purpose, the knob 1002 can include an internal pinion gear 1004 (FIG. 58) that engages teeth of a rack on the drive mechanism 904. In this manner, rotation of the knob 1002 causes corresponding axial movement of the drive mechanism and the inner shaft.

Figure 58:
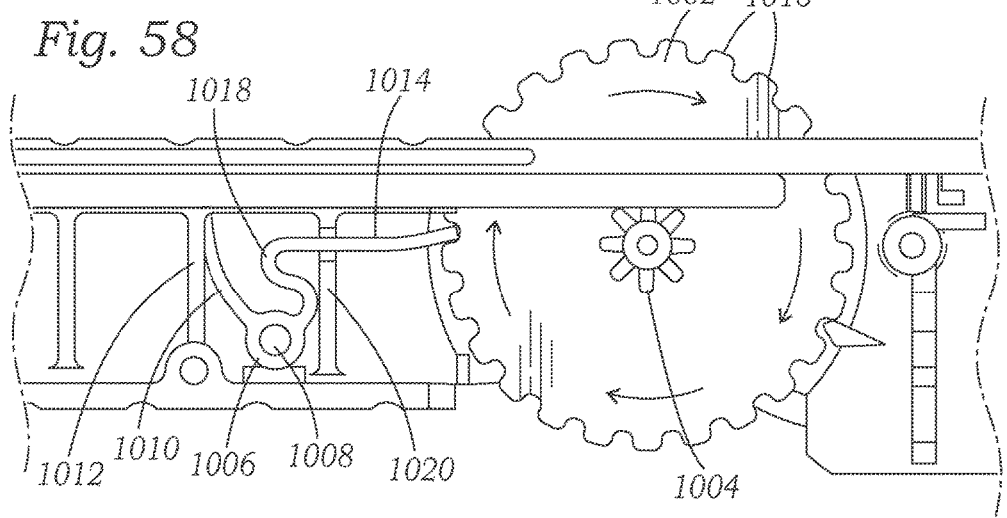
FIG. 58 is an enlarged view of the inside of the handle of FIG. 57.

As the knob 1002 is rotated to expose the implant, the outer shaft 900 is stretched elastically and the inner shaft 906 is compressed elastically. The forces on the inner and outer shafts impart a force on the knob 1002 that urges the knob in a direction opposite the rotational force applied to the knob by the user. Removal of manual pressure from the knob can cause "spring-back" of the sheath, pulling the implant back into the sheath. Referring to FIG. 58, to better control deployment of the implant, a biasing member, such as the illustrated spring 1006, can be employed to increase the friction on the knob 1002. The spring 1006 is mounted on a pin 1008 within the handle 1000. The spring 1006 comprises a first spring portion 1010 that bears against an adjacent surface 1012 inside the handle, a second spring portion 1014 positioned to engage nubs, or ribs, 1016, spaced around the outer surface of the knob 1002, and a third, S-shaped intermediate portion 1018 that bears against an adjacent surface 1020 inside the handle. The second spring portion 1014 is long enough to contact each of the ribs 1016 as the knob is rotated but not the outer surface of the knob between adjacent ribs. Due to the curvature of the intermediate portion 1018, the second spring portion 1014 has a greater resistance when it is deflected downwardly compared to when it is deflected upwardly. In use, when the knob is rotated in a first direction to advance the inner shaft 906 to deploy the support stent (clockwise in FIG. 58), the second spring portion 1014 is deflected slightly upwardly each time one of the ribs 1016 on the knob comes into contact with the spring portion 1014. The action of the ribs 1016 pushing upwardly on the spring portion 1014 as the knob is rotated provides the user with tactile feedback regarding the degree of rotation of the knob, which corresponds to the degree of advancement of the implant from the sheath. The contact between the ribs 1016 and the spring portion 1014 also generates an audible "clicking" sound, thereby providing audible feedback to the user. If manual pressure on the knob is reduced or released during the deployment phase, the forces imparted on the knob due to elastic deformation of the outer and inner shafts 900, 906 is resisted by the spring force of the spring portion 1014 acting on the knob in the opposite direction. In other words, if the elastic deformation of the shafts urges the knob in the counterclockwise direction in FIG. 58, the biasing force of the spring portion 1014 can counteract that movement and prevent rotation of the knob in the counterclockwise direction, which would otherwise cause the implant to be drawn back into the sheath 902. As noted above, the spring portion 1014 has a greater resistance when it is deflected downwardly compared to when it is deflected upwardly. Thus, the spring portion 1014 provides a greater resistance against rotation of the knob for counterclockwise rotation as compared to its resistance against rotation for clockwise rotation. The spring therefore can be said to provide asymmetric friction control of the knob, which allows relatively easy rotation of the knob for deployment of the implant (in the clockwise direction in the illustrated embodiment) and increases the resistance on the knob in the opposite direction to prevent "spring back" of the inner shaft relative to the outer shaft.

In alternative embodiments, other types of biasing members can be used to apply resistance against rotation of the knob, such as torsion springs, elastomeric members, etc.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating aortic insufficiency, comprising:
   delivering a support structure to a position on or adjacent to a surface of the outflow side of a native heart valve of a patient, the support structure comprising an annular metal frame defining an interior and at least one projection comprising a non-metallic material and extending radially inwardly from the metal frame;
   positioning the support structure around the leaflets of the native heart valve such that the leaflets of the native heart valve are located within the interior of the metal frame;
   advancing an expandable prosthetic heart valve into the native heart valve and into the interior of the metal frame, the prosthetic heart valve comprising a radially expandable annular frame defining a plurality of openings; and
   expanding the expandable prosthetic heart valve into contact with the leaflets of the native valve, thereby causing the leaflets of the native valve to be frictionally secured between an inner surface of the metal frame and an outer surface of the prosthetic heart valve and causing the at least one projection and a portion of one of the leaflets contacted by the at least one projection to extend into one of said openings of the frame of the prosthetic heart valve;
   wherein the metal frame comprises a plurality of struts and a pair of apertures formed in at least one of the struts, and the at least one projection comprises a wound or knotted ball of suture material disposed radially inwardly relative to the at least one of the struts, and two suture tails extending from opposite sides of the wound or knotted ball, wherein the suture tails are threaded radially outwardly through the pair of apertures and tied to each other at a location radially outwardly relative to the at least one of the struts to secure the at least one projection to the at least one of the struts.

2. The method of claim 1, wherein the metal frame comprises an inflow end and an outflow end, and the at least one projection is located along the length of the metal frame between the inflow and outflow ends.

3. The method of claim 1, wherein the at least one projection comprises a plurality of projections extending radially inwardly from the metal frame, and when the prosthetic heart valve is expanded to contact the leaflets of the native valve, each projection and a portion of one of the leaflets contacted by the projection are caused to extend into one of said openings of the frame.

4. The method of claim 1, wherein the act of advancing the prosthetic valve into the native heart valve is performed after the support structure is positioned around the leaflets of the native heart valve and while the support structure is maintained in a substantially fixed position relative to the native heart valve.

5. An assembly for treating aortic insufficiency, comprising:

a prosthetic heart valve configured to be implanted within a native heart valve, the prosthetic heart valve comprising a radially expandable annular frame defining a plurality of openings; and a support stent configured to be implanted around native leaflets of the native heart valve such that the native leaflets can be frictionally secured between the support stent and the prosthetic heart valve, the support stent comprising an annular metal frame that defines one or more peaks and one or more valleys along its circumference, the support stent frame being radially compressible into a compressed state and self-expandable into an uncompressed state, the support stent further comprising at least one projection comprising a non-metallic material, the at least one projection extending radially inwardly from the support stent frame and configured to press a portion of one of the native leaflets into one of the openings of the frame of the prosthetic heart valve, wherein the metal frame comprises a plurality of struts and a pair of apertures formed in at least one of the struts, wherein the at least one projection comprises a knotted or wound ball of suture material disposed radially inwardly relative to the at least one of the struts, and two suture tails extending from opposite sides of the knotted or wound ball, wherein the suture tails are threaded radially outwardly through the pair of apertures and tied to each other at a location radially outwardly relative to the at least one of the struts to secure the at least one projection to the at least one of the struts.

6. The assembly of claim 5, wherein the support stent is sized such that it can be positioned within the aorta of a patient at a location adjacent to the aortic valve and thereby circumscribe the native leaflets of the aortic valve.

7. The assembly of claim 5, wherein the support stent further comprises a fabric cover covering the support stent frame and the at least one projection.

8. The assembly of claim 5, wherein the support stent includes an inflow end and an outflow end, and the at least one projection is located along a length of the support stent between the inflow and outflow ends.

9. The assembly of claim 5, wherein the at least one projection comprises a plurality of projections extending radially inwardly from the annular metal frame of the support stent, and wherein the plurality of projections are configured such that, when the prosthetic heart valve is expanded to contact the native leaflets of the native heart valve, each of the plurality of projections and a portion of one of the native leaflets are caused to extend into one of the plurality of openings of the annular frame of the prosthetic heart valve, wherein each projection is secured to one of the struts of the metal frame with two respective suture tails extending outwardly through a pair of apertures in the corresponding strut.

10. The assembly of claim 5, wherein the knotted or wound ball comprises a triple wrap knot formed by a multi-stranded suture knit or braid.

11. The assembly of claim 5, wherein the at least one of the struts comprises a plurality of pairs of apertures and the at least one projection comprises a plurality of knotted or wound balls, each of which is secured to a respective pair of apertures.

12. The assembly of claim 5, wherein the at least one projection comprises a knotted ball of suture material.

13. An assembly for treating aortic insufficiency, comprising:

a prosthetic heart valve configured to be implanted within a native heart valve, the prosthetic heart valve comprising a radially expandable annular frame defining a plurality of openings; and a support stent configured to be implanted around native leaflets of the native heart valve such that the native leaflets can be frictionally secured between the support stent and the prosthetic heart valve, the support stent comprising an annular metal frame comprising a plurality of struts arranged to define one or more peaks and one or more valleys along a circumference of the frame, the support stent frame being radially compressible into a compressed state and self-expandable into an uncompressed state;

wherein the support stent further comprises a plurality of projections comprising a non-metallic material, the plurality of projections extending radially inwardly from the struts of the metal frame, wherein the plurality of projections are configured such that, when the prosthetic heart valve is expanded to contact the native leaflets of the native heart valve, each of the plurality of projections and a portion of one of the native leaflets are caused to extend into one of the plurality of openings of the annular frame of the prosthetic heart;

wherein each projection comprises a knotted or wound ball of suture material disposed radially inwardly relative to an adjacent strut of the metal frame, and two suture tails extending from opposite sides of the knotted or wound ball and threaded radially outwardly through respective apertures in the adjacent strut, with the suture tails being tied to each other at a location radially outwardly relative to the adjacent strut to secure the knotted or wound ball of suture material to the adjacent strut;

wherein the projections are secured to respective struts at locations between opposing ends of the struts;

wherein the support stent further comprises a fabric cover covering the struts and the projections.

14. The assembly of claim 13, wherein each projection comprises a knotted ball of suture material.

* * * * *